(12) United States Patent
Conrad et al.

(10) Patent No.: US 10,493,131 B2
(45) Date of Patent: Dec. 3, 2019

(54) MATERIALS AND METHODS FOR MODULATING ACTIVITY OF BONE MARROW DERIVED CELLS

(75) Inventors: Kirk P. Conrad, Gainesville, FL (US); Mark S. Segal, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 919 days.

(21) Appl. No.: 14/240,842

(22) PCT Filed: Aug. 30, 2012

(86) PCT No.: PCT/US2012/053033
§ 371 (c)(1),
(2), (4) Date: Apr. 28, 2014

(87) PCT Pub. No.: WO2013/033324
PCT Pub. Date: Mar. 7, 2013

(65) Prior Publication Data
US 2014/0242074 A1 Aug. 28, 2014

Related U.S. Application Data

(60) Provisional application No. 61/529,662, filed on Aug. 31, 2011.

(51) Int. Cl.
| | | |
|---|---|---|
| *A61K 35/28* | (2015.01) | |
| *A61K 35/26* | (2015.01) | |
| *A01N 25/00* | (2006.01) | |
| *A61K 38/22* | (2006.01) | |
| *C07K 16/26* | (2006.01) | |
| *C07K 16/28* | (2006.01) | |
| *C12N 15/113* | (2010.01) | |

(52) U.S. Cl.
CPC .......... *A61K 38/2221* (2013.01); *C07K 16/26* (2013.01); *C07K 16/2869* (2013.01); *C12N 15/1136* (2013.01); *C12N 15/1138* (2013.01)

(58) Field of Classification Search
None
See application file for complete search history.

(56) References Cited

U.S. PATENT DOCUMENTS

| | | | | |
|---|---|---|---|---|
| 5,712,392 | A * | 1/1998 | Thurkauf | C07D 233/64 544/295 |
| 6,723,702 | B2 * | 4/2004 | Conrad | A61K 38/2221 424/198.1 |
| 6,780,836 | B2 * | 8/2004 | Unemori | A61K 38/2221 435/69.1 |
| 7,339,032 | B2 | 3/2008 | Ramanathan et al. | |
| 7,553,813 | B2 | 6/2009 | Unemori | |
| 7,582,297 | B2 * | 9/2009 | Reed | A61K 45/06 424/130.1 |
| 9,119,833 | B2 * | 9/2015 | Parry | A61K 38/2221 |
| 9,359,422 | B2 * | 6/2016 | Rosengren | C07K 14/64 |
| 2001/0044413 | A1 | 11/2001 | Pierce et al. | |
| 2002/0019349 | A1 | 2/2002 | Conrad et al. | |
| 2004/0005306 | A1 | 1/2004 | Loscalzo et al. | |
| 2004/0266685 | A1 * | 12/2004 | Conrad | A61K 38/2221 514/8.1 |
| 2006/0052304 | A1 * | 3/2006 | Stewart | A61K 38/2221 514/11.3 |
| 2006/0247172 | A1 * | 11/2006 | Unemori | A61K 38/2221 514/5.3 |
| 2006/0264367 | A1 | 11/2006 | Samuel et al. | |
| 2008/0300172 | A1 * | 12/2008 | Yue | A61K 38/2221 514/1.1 |
| 2013/0012441 | A1 * | 1/2013 | Stewart | C07K 16/26 514/12.7 |
| 2013/0237481 | A1 * | 9/2013 | Kraynov | C07K 14/64 514/12.7 |
| 2016/0287672 | A1 * | 10/2016 | Unemori | A61K 38/2221 |
| 2017/0035897 | A1 * | 2/2017 | Kraynov | C07K 14/64 |

FOREIGN PATENT DOCUMENTS

| | | | |
|---|---|---|---|
| WO | WO 2005/115435 A2 | 12/2005 | |
| WO | WO 2009/140657 A2 | 11/2009 | |

OTHER PUBLICATIONS

Anasetti, Claudio et al. "Peripheral-Blood Stem Cells versus Bone Marrow from Unrelated Donors," *New England Journal of Medicine*, 2012; vol. 367, No. 16, p. 1487-1496.
Bani, Daniele, "Relaxin as a Natural Agent for Vascular Health," *Vascular Health and Risk Management*, 2008, vol. 4, No. 3, p. 515-524.
Carmeliet, Peter, "Angiogenesis in Life, Disease, and Medicine," *Nature Publishing Group*, 2005, vol. 438, No. 15, p. 932-936.
Carmeliet, Peter, "Angiogenesis in Life, Disease, and Medicine [Supplemental Material]," *Nature Publishing Group*, 2005, vol. 438, No. 15, p. 1-14. Retrieved from http://www.nature.com.
Conrad, Kirk P. "Pregnancy and Relaxin: Vasodilatory Responses and Mechanisms," [PowerPoint slides].
Founds, Sandra A. et al. "Gene Expression in First Trimester Preeclampsia Placenta," *Biological Research for Nursing*, 2011, vol. 13, No. 2, p. 134-139.
Founds, Sandra A. et al. "LAIR2 Localizes Specifically to Sites of Extravillous Trophoblast Invasion," *Placenta*, 2010, vol. 31, p. 880-885.
Inoue, Teruo, "Mobilization of CD34-Positive Bone Marrow-Derived Cells After Coronary Stent Implantation: Impact on Restenosis," *Circulation*, 2006, vol. 115, p. 553-561.

(Continued)

*Primary Examiner* — Michail A Belyavskyi
(74) *Attorney, Agent, or Firm* — Timothy H. Van Dyke; Beusse, Wolter, Sanks & Maire PLLC

(57) ABSTRACT

The subject invention provides methods for recruitment of bone marrow-derived cells, including bone marrow-derived endothelial cells (BMDEC), and increasing their function by administration of relaxin. The methods of the invention can be used in, for example, treating conditions amenable to treatment by recruitment of bone marrow-derived cells, such as BMDEC and bone marrow-derived angio-osteogenic progenitor cell.

15 Claims, 14 Drawing Sheets

(56) References Cited

OTHER PUBLICATIONS

Penn, Mark et al. "Genetic Enhancement of Stem Cell Engraftment, Survival, and Efficacy," *Circulation Research*, 2008, vol. 102, p. 1471-1482.

Rotmans, Joris I et al. "Endothelial progenitor cell-seeded grafts: Rash and risky," *Canadian Journal of Cardiology*, 2006, vol. 22, No. 11, p. 1113-1116.

Segal, Mark S. et al. "Relaxin Increases Human Endothelial Progenitor Cell NO and Migration and Vasculogenesis in Mice," *Blood*, 2012, vol. 119, p. 629-636.

Sen, Shaundeep et al. "Endothelial Progenitor Cells: Novel Biomarker and Promising Cell Therapy for Cardiovascular Disease," *Clinical Science*, 2011, vol. 120, p. 263-283.

Szmitko, Paul E. et al. "Endothelial Progenitor Cell-Coated Stents Under Scrutiny," *Canadian Journal of Cardiology*, 2006, vol. 22, No. 13, p. 1117-1119.

\* cited by examiner

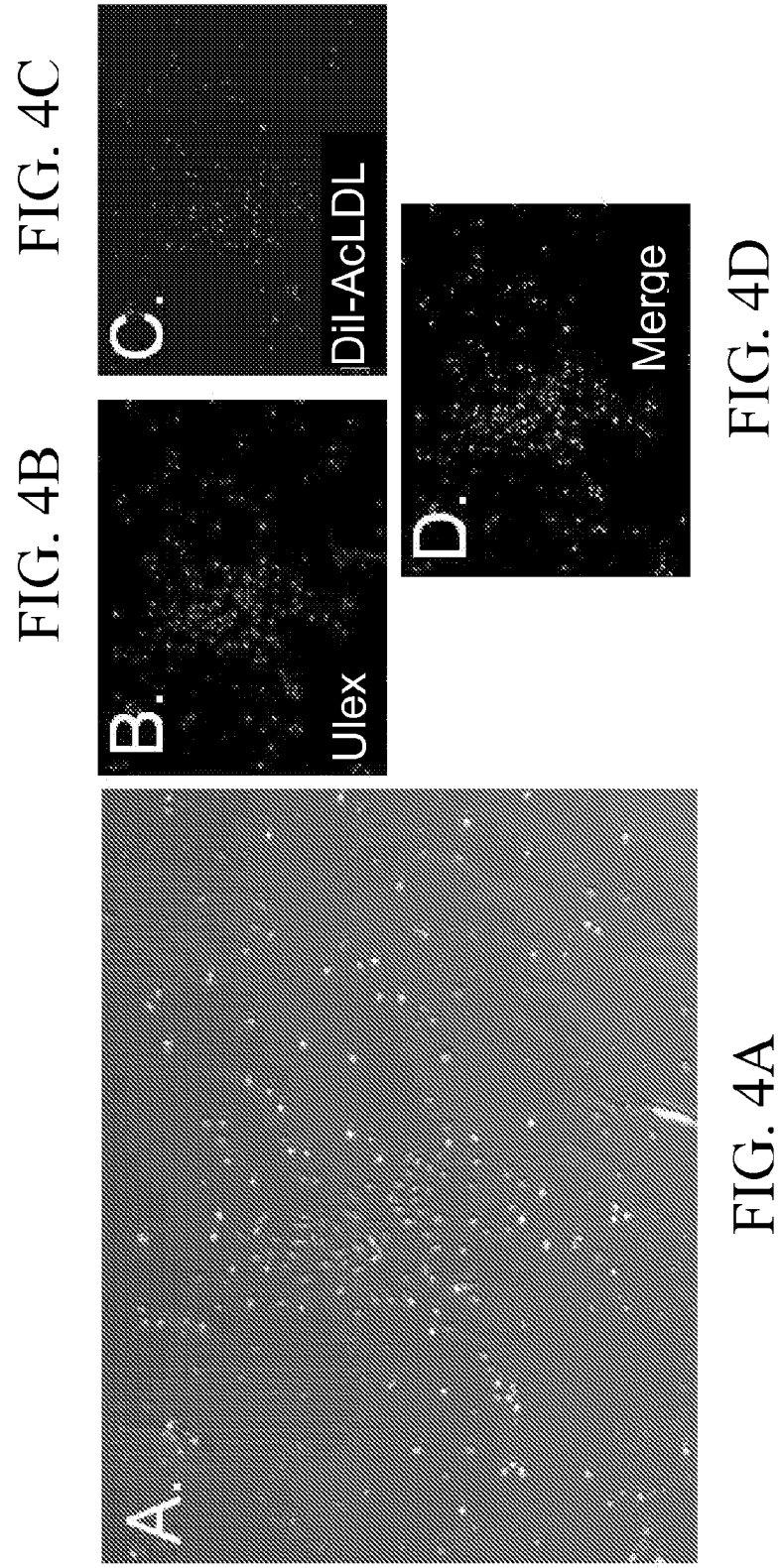

MATERIALS AND METHODS FOR MODULATING ACTIVITY OF BONE MARROW DERIVED CELLS

CROSS-REFERENCE TO RELATED APPLICATIONS

This application is a National Stage Application of international Application Number PCT/US12/053033, filed. Aug. 30, 2012; which claims the benefit of U.S. Provisional Patent Application Ser. No. 61/529,662, filed Aug. 31, 2011, the disclosures of which is are hereby incorporated by reference in its their entirety, including all figures, tables or drawings.

GOVERNMENT SUPPORT

This invention was made with government support under grant numbers HL067937, HD037067, EY012601, and EY007739 awarded by the National Institutes of Health. The government has certain rights in the invention.

BACKGROUND OF INVENTION

Dramatic changes in systemic and renal hemodynamics occur during pregnancy. There is a marked decrease in systemic vascular resistance and reciprocal increases in cardiac output and global arterial compliance, accompanied by a modest decline in mean arterial pressure. The renal circulation participates in this maternal vasodilatory response, and consequently, renal plasma flow and glomerular filtration rate rise by 80 and 50%, respectively. Although the mechanisms underlying these maternal adaptations to pregnancy are not fully understood, there is increasing evidence that the ovarian peptide hormone relaxin plays a key role (reviewed in Conrad, K. P, 2011 "Emerging role of relaxin in the maternal adaptations to normal pregnancy: implications for preeclampsia" *Semin Nephrol.* 31(1):15-32).

Originally isolated from the ovary by Hisaw and colleagues, relaxin was named for its ability to relax the pubis symphysis in some species (Hisaw, F, 1926 "Experimental relaxation of the public ligament of the guinea pig" *Proc Exp Biol Med* 23:661-663). In non-human primates, it was subsequently shown to cause morphological changes in endothelial cells of endometrial blood vessels consistent with vascular hypertrophy and hyperplasia, and enlargement of arterioles and capillaries (Hisaw, F. L., Hisaw, F. L., Jr., and Dawson, A. B, 1967 "Effects of relaxin on the endothelium of endometrial blood vessels in monkeys (*Macaca mulatta*)" *Endocrinology* 81:375-385).

Relaxin circulates at low levels in the luteal phase of the menstrual cycle, and in pregnancy peaks during the first trimester falling to intermediate levels thereafter (Sherwood, O., 1994, *Relaxin*. NY: Raven. 861-1009 pp.). Previously relaxin was shown to augment MCP-1-induced monocyte chemotaxis, but was not a monocyte chemoattractant by itself (Figueiredo, K. A., Mui, A. L., Nelson, C. C., and Cox, M. E. 2006. Relaxin Stimulates Leukocyte Adhesion and Migration through a Relaxin Receptor LGR7-dependent Mechanism. *J. Biol. Chem.* 281:3030-3039).

Humans have three relaxin genes designated relaxin-1, -2 and -3 (Sherwood, O. D, 2004, "Relaxin's physiological roles and other diverse actions" *Endocr Rev* 25:205-234). Rats and mice each have two relaxin genes designated relaxin-1 and -3. Human relaxin-2, as well as rat and mouse relaxin-1 gene products are true orthologs, insofar as they are secreted by the corpus luteum during pregnancy and circulate. Humans, rats and mice have a relaxin receptor, the LGR7 (leucine rich repeat-containing G protein coupled) receptor recently renamed relaxin/insulin-like family peptide 1 receptor, RXFP1. Human relaxin may also bind to the LGR8 receptor (RXFP2), albeit with reduced affinity (Sudo S et al. 2003 "H3 relaxin is a specific ligand for LGR7 and activates the receptor by interacting with both the actodomain and the exoloop 2," *J Biol Chem.*, 278(10):7855-7862). Recently, two new receptors have been described for relaxin-3, GPCR135 and 142 (Chen, J., Kuei, C., Sutton, S. W., Bonaventure, P., Nepomuceno, D., Eriste, E., Sillard, R., Lovenberg, T. W., and Liu, C, 2005, "Pharmacological characterization of relaxin-3/INSL7 receptors GPCR135 and GPCR142 from different mammalian species" *J Pharmacol Exp Ther* 312:83-95), although GPCR142 is a pseudogene in rats.

Infusion of recombinant human relaxin-2 (rhRLX) in nonpregnant conscious female and male rats significantly decreases renal and systemic vascular resistances, and increases cardiac output, renal blood flow, glomerular filtration, and global arterial compliance, thus mimicking the circulatory changes of pregnancy (Conrad, K. P., 2011 "Emerging role of relaxin in the maternal adaptations to normal pregnancy: implications for preeclampsia," *Semin Nephrol.*, 31(1):15-32). Conversely, administration of relaxin-neutralizing antibodies or ovariectomy inhibits the circulatory changes during midterm pregnancy in conscious rats (Conrad, K. P., *Semin Nephrol. supra*)). In addition to reductions in arterial tone and/or arterial compositional or geometrical remodeling, another likely mechanism for the decrease in systemic vascular resistance (SVR) and increase in global arterial compliance (AC) observed during relaxin administration or in pregnancy is increased angiogenesis (Conrad, K. P., Debrah, D. O., Novak, J., Danielson, L. A., and Shroff, S. G., 2004, "Relaxin modifies systemic arterial resistance and compliance in conscious, nonpregnant rats" *Endocrinology* 145:3289-3296).

Bone marrow derived endothelial cells (BMDEC) integrate into the vascular wall either differentiating into endothelial cells (vasculogenesis) or serving a paracrine role in stimulating local angiogenesis or endothelial repair. The number of CD34+ BMDEC expressing vascular endothelial growth factor receptor (VEGFR)-2 that circulate in the bloodstream is an independent predictor of early subclinical atherosclerosis in healthy subjects (Fadini, G. P., Coracina, A., Baesso, I., Agostini, C., Tiengo, A., Avogaro, A., and Vigili de Kreutzenberg, S. 2006. Peripheral Blood CD34+ KDR+ Endothelial Progenitor Cells Are Determinants of Subclinical Atherosclerosis in a Middle-Aged General Population. *Stroke* 37:2277-2282; Chironi, G., Walch, L., Pernollet, M.-G., Gariepy, J., Levenson, J., Rendu, F., and Simon, A. Decreased number of circulating CD34+KDR+ cells in asymptomatic subjects with preclinical atherosclerosis. *Atherosclerosis* In Press, Corrected Proof), inversely proportional to the risk factors for atherosclerosis (Vasa, M., Fichtlscherer, S., Aicher, A., Adler, K., Urbich, C., Martin, H., Zeiher, A. M., and Dimmeler, S. 2001. Number and migratory activity of circulating endothelial progenitor cells inversely correlate with risk factors for coronary artery disease. *Circ Res* 89:E1-7), and predicts future cardiovascular events (Schmidt-Lucke, C., Rossig, L., Fichtlscherer, S., Vasa, M., Britten, M., Kamper, U., Dimmeler, S., and Zeiher, A. M. 2005. Reduced Number of Circulating Endothelial Progenitor Cells Predicts Future Cardiovascular Events: Proof of Concept for the Clinical Importance of Endogenous Vascular Repair. *Circulation* 111:2981-2987).

Several studies have indirectly addressed the role of circulating BMDEC in postnatal vasculogenesis (Crosby, J. R., Kaminski, W. E., Schatteman, G., Martin, P. J., Raines, E. W., Seifert, R. A., and Bowen-Pope, D. F. 2000. Endothelial cells of hematopoietic origin make a significant contribution to adult blood vessel formation. *Circ Res* 87:728-730).

The number of circulating BMDEC in patients with both type I (quantifying by CFU) and type II (CD34+, VEGFR2+ cells measured by flow cytometry) diabetes is significantly reduced as compared with healthy subjects (Loomans, C. J. M., de Koning, E. J. P., Staal, F. J. T., Rookmaaker, M. B., Verseyden, C., de Boer, H. C., Verhaar, M. C., Braam, B., Rabelink, T. J., and van Zonneveld, A.-J. 2004. Endothelial Progenitor Cell Dysfunction: A Novel Concept in the Pathogenesis of Vascular Complications of Type 1 Diabetes. *Diabetes* 53:195-199; Werner, N., Kosiol, S., Schiegl, T., Ahlers, P., Walenta, K., Link, A., Bohm, M., and Nickenig, G. 2005. Circulating Endothelial Progenitor Cells and Cardiovascular Outcomes. *N Engl J Med* 353:999-1007). In addition, in vitro protocols used to evaluate the functional characteristics of diabetic BMDEC have demonstrated defective adherence (Fadini, G., Sartore, S., Schiavon, M., Albiero, M., Baesso, I., Cabrelle, A., Agostini, C., and Avogaro, A. 2006. Diabetes impairs progenitor cell mobilisation after hindlimb ischaemia-reperfusion injury in rats. *Diabetologia* 49:3075-3084; Capla, J. M., Grogan, R. H., Callaghan, M. J., Galiano, R. D., Tepper, O. M., Ceradini, D. J., and Gurtner, G. C. 2007. Diabetes impairs endothelial progenitor cell-mediated blood vessel formation in response to hypoxia. *Plast Reconstr Surg* 119:59-70), decreased ability to form tubes (Loomans, C. J. M., de Koning, E. J. P., Staal, F. J. T., Rookmaaker, M. B., Verseyden, C., de Boer, H. C., Verhaar, M. C., Braam, B., Rabelink, T. J., and van Zonneveld, A.-J. 2004. Endothelial Progenitor Cell Dysfunction: A Novel Concept in the Pathogenesis of Vascular Complications of Type 1 Diabetes. *Diabetes* 53:195-199; Tepper, O. M., Galiano, R. D., Capla, J. M., Kalka, C., Gagne, P. J., Jacobowitz, G. R., Levine, J. P., and Gurtner, G. C. 2002. Human Endothelial Progenitor Cells From Type II Diabetics Exhibit Impaired Proliferation, Adhesion, and Incorporation Into Vascular Structures. *Circulation* 106: 2781-2786), and reduction in proliferative capacity (Tepper, O. M., Galiano, R. D., Capla, J. M., Kalka, C., Gagne, P. J., Jacobowitz, G. R., Levine, J. P., and Gurtner, G. C. 2002. Human Endothelial Progenitor Cells From Type II Diabetics Exhibit Impaired Proliferation, Adhesion, and Incorporation Into Vascular Structures. *Circulation* 106:2781-2786).

Fetal endothelial progenitor cells contribute to maternal angiogenesis during pregnancy (Nguyen Huu, S., Oster, M., Uzan, S., Chareyre, F., Aractingi, S., and Khosrotehrani, K. 2007. Maternal neoangiogenesis during pregnancy partly derives from fetal endothelial progenitor cells. *Proc Natl Acad Sci USA* 104:1871-1876). It is also possible that BMDECs participate in uterine vascular remodeling during gestation. Robb et al. hypothesized that since BMDECs may have a homeostatic role in maintaining both the maternal systemic and uterine vasculature, BMDEC may be the link between cardiovascular risk factors and increased risk of pre-eclampsia (Robb, A. O., Mills, N. L., Newby, D. E., and Denison, F. C. 2007. Endothelial progenitor cells in pregnancy. *Reproduction* 133:1-9).

However, endothelial progenitor cells are not abundant in either circulating blood or the bone marrow. In fact, the low abundance of endothelial progenitor cells represents one of the critical issues to overcome in the clinical application of endothelial progenitor cells. (Kawamoto et al. (2007) Catheterization and Cardiovascular Interventions 70:477-484.) Increased endothelial progenitor cell levels in the clinic currently are achieved by transplantation, which involves isolating endothelial progenitor cells from a donor, expanding the endothelial progenitor cells ex vivo, and then transplanting the endothelial progenitor cells to the recipient. Endothelial progenitor cell transplantation is an invasive and expensive procedure, and the ex vivo manipulation of isolated endothelial progenitor cells poses various health risks, such as transmission of infectious agents, to both the patient and care provider.

Failed or delayed fracture healing is a major clinical problem, and is mainly due to poor vascularization. Healing of bone fractures normally occurs within 8-12 weeks in healthy humans. However, a significant proportion of bone fractures fail to properly heal, i.e., non-union. A rate-limiting step in the healing process is blood flow, which is impeded by concomitant disruption of the bone vasculature. In addition, blood flow to the bone may be impaired at baseline before injury in the elderly, diabetics and smokers. The immobility resulting from bone fractures especially in the elderly is frequently fatal due to subsequent venous stasis, thrombosis and pulmonary embolism.

Neoangiogenesis is essential to bone healing. When disrupted by the angiogenic inhibitor TNP-470 normal osteogenesis was prevented resulting in pathologic fibrous union [Fang T D et al. 2005. Angiogenesis is required for successful bone induction during distraction osteogenesis. *J Bone Miner Res.* 20:1114-24]. Recent evidence shows that by enhancing mobilization of bone marrow progenitor cells, bone healing is accelerated in mice [Wang X X et al., 2011, Progenitor cell mobilization enhances bone healing by means of improved neovascularization and osteogenesis. *Plast Reconstr Surg.* 128:395-405; Matsumoto T et al., 2008, Fracture induced mobilization and incorporation of bone marrow-derived endothelial progenitor cells for bone healing. *J Cell Physiol.* 215:234-42; and Matsumoto T et al., 2006, Therapeutic potential of vasculogenesis and osteogenesis promoted by peripheral blood CD34− positive cells for functional bone healing. *Am J Pathol.* 169:1440-57]. Further increase was observed following their mobilization from bone by AMD-3100, which was associated with accelerated bone healing [Wang X X et al., 2011, ibid.].

The administration of human CD34+ cells to nude mice with experimentally induced fractures demonstrated enhanced vascularization, perfusion and bone healing associated with human specific markers for both endothelial cells and osteoblasts at the fracture site [Matsumoto T et al., 2006, ibid.]. In chimeric mice stably transplanted with bone marrow harvested from donors expressing LacZ regulated by the Tie-2 promoter, the same investigators demonstrated β-galactosidase staining at the fracture site [Matsumoto T et al., 2008, ibid.]. Taken together, these studies suggest an important role for vasculogenesis and osteogenesis mediated by bone marrow derived progenitor cells.

There is a need for methods effective at increasing bone marrow derived cells, including BMDEC and/or bone marrow-derived angio-osteogenic progenitor cell levels in the blood that do not require costly or invasive isolation or transplantation procedures. The present invention meets this need by providing novel methods useful for increasing bone marrow derived cells, particularly BMDEC mobilization.

BRIEF SUMMARY

The subject invention, which provides therapeutic materials and methods, is based on the determination that relaxin regulates the biology of bone marrow derived cells. For example, with BMDEC, relaxin regulates BMDEC in several ways: (a) increases intracellular nitric oxide (NO) levels in BMDEC; (b) is a chemoattractant for BMDEC; (c) mobilizes BMDEC; and (d) enhances BMDEC integration into sites of vasculogenesis. These effects of relaxin are mediated by the major relaxin receptor, RXFP1, and not the RXFP2 receptor.

Advantageously, relaxin mobilizes and activates BMDEC without being pro-inflammatory and, may act as an anti-inflammatory. This makes relaxin the only cytokine known to positively impact BMDEC number and function without being pro-inflammatory, which offers a distinct advantage for relaxin as a potent therapeutic.

Relaxin robustly stimulates intracellular NO generation in human BMDEC, mediated via the PI3/Akt pathway, and dramatically enhances BMDEC mobilization and neovascularization. These actions of relaxin on BMDEC provide an additional cellular mechanism for the decrease in systemic vascular resistance and increase in global arterial compliance via promotion of angiogenesis/vasculogenesis in maternal organs such as the pancreas and breast, as well as arterial remodeling observed during healthy pregnancies and a novel explanation for the increased risk of preeclampsia in diabetic patients.

In one aspect the subject invention provides a method for mobilizing, activating and incorporating BMDEC to enhance angiogenesis and/or vasculogenesis, and to cause an increase in blood flow. Thus relaxin can be used to treat and/or prevent diseases and/or conditions amenable to treatment by recruitment of BMDEC and/or by increased production of NO. Alternatively, relaxin can be used to contribute to maternal vasculogenesis during pregnancy, which in turn can abet gestational decrease in systemic vascular resistance and increase in global arterial compliance.

In another aspect, the invention provides a method of preserving function and long-term patency of dialysis access.

The invention also provides a method for treating ischemia suffered by an organ (e.g., brain, bowel, skin, limb, bone, etc.), such as aseptic necrosis of the femoral head, uteroplacental or fetoplacental ischemia.

In yet another aspect, the invention provides a method for treating bone fracture and for improving recovery after bone surgery. A rate-limiting step to healing bone is disruption of blood supply, especially in the periosteum. Healing of bones in the elderly is especially retarded due in part to poor blood supply. According to the subject invention, relaxin can be used for attracting BMDEC to induce increased blood flow and angiogenesis and/or vasculogenesis in the context of bone repair. In a related aspect, relaxin can be effective in this regard through increasing the number and/or activity of circulating bone marrow derived angio-osteoblastic cells.

The subject invention also provides a method for treating central and peripheral nervous system diseases and neuropathies associated with reduced blood flow (e.g., Alzheimer's disease, vascular dementia, and Parkinson's disease).

The invention also provides a method for improving embryo implantation and/or placentation in a mother by increasing the number of blood vessels in the endometrium. In addition, the invention provides a method for improving embryo development and fetal growth. In particular, the subject invention provides methods for promoting and improving fetoplacental and fetal vasculature.

Another aspect of the invention provides a method for improving the function of an organ graft following implantation including heart, kidney and skin. In a related aspect, the invention provides a method for treating pancreatic beta-cell injury, particularly to facilitate the recovery of injured beta-cells or to improve the survival and/or function of islet and/or pancreas allografts.

Yet another aspect of the invention provides a method for facilitating adaptation to high altitude or otherwise low oxygen environments.

Another embodiment of the invention provides a method for improving skeletal muscle angiogenesis and/or vasculogenesis and blood flow for athletes, and in muscular dystrophy.

The subject invention also provides methods for modulating BMDEC mobilization and integration in a subject in need thereof by administering an effective amount of a compound to block relaxin activity. In a related embodiment, the compound that blocks relaxin activity also reduces or inhibitis vasculogenesis. In one embodiment, the compound is a relaxin antagonist that inhibits binding of relaxin to relaxin receptor Rxfp1.

DETAILED DISCLOSURE

Figure 1A:
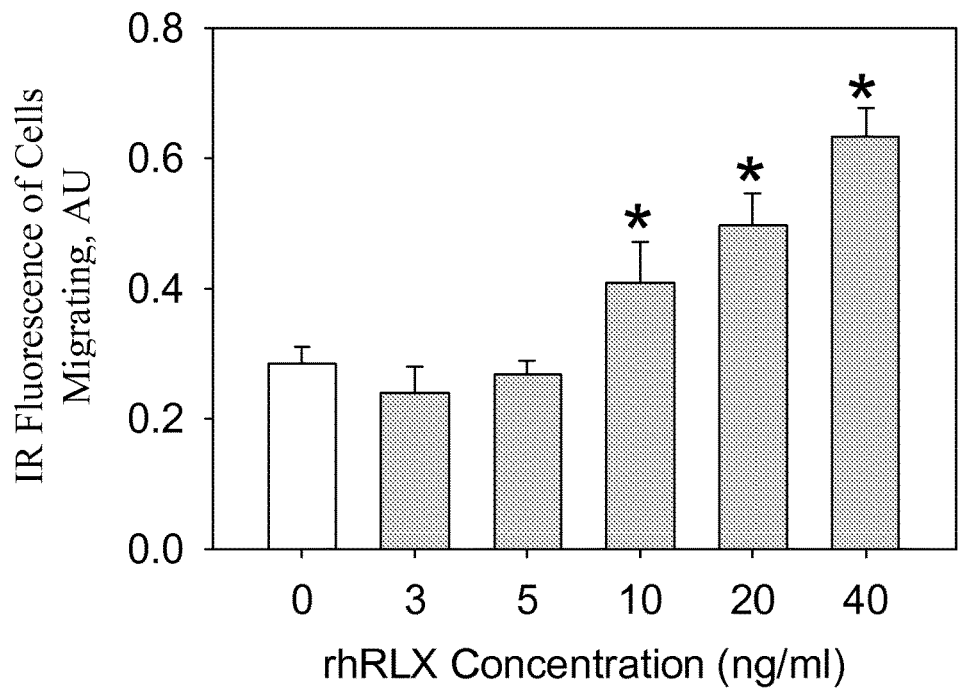
FIG. 1. Relaxin is a chemoattractant for CD34+ BMDEC migration. (A) CD34+ BMDEC migrate to increasing concentrations of rhRLX. *$p<0.001$ versus 0 ng/ml rhRLX. Each bar depicts the mean (±SD) infrared (IR) fluorescence of migrating cells from 4 wells per rhRLX concentration. Shown is a representative of 4 experiments. (B) CD34+ BMDEC from 10-healthy individuals that migrate to rhRLX (50 ng/ml) and SDF-1 (100 nM) is expressed as mean percentage (±SD) of cells in the lower chamber, above background migration. *$p<0.029$ versus SDF-1. (C) CD34+ BMDEC were seeded in the upper Boyden chamber with either vehicle or 60 ng/ml of rhRLX in the top and/or bottom as indicated. Shown is mean percentage (±SD of 3 wells) of CD34+ BMDEC loaded to the top chamber that have migrated, after subtracting background. *$p<0.025$ versus black bar.

In accordance with the subject invention, relaxin has been found to be a chemoattractant, but not a chemokinetic agent, increasing directional CD34+ BMDEC migration in a NO—dependent manner. Thus, relaxin is a novel regulator of BMDEC number and function, and is therapeutically useful in treating conditions amenable to treatment by recruitment of BMDEC, which abet local vasculogenesis and/or increased blood flow. As understood by the skilled artisan, vasculogenesis refers to the formation of new blood vessels de novo.

Recombinant human relaxin-2 (rhRLX) stimulates PI3 kinase/Akt B-dependent NO production in human BMDEC within minutes, and activates BMDEC migration that is inhibited by L—$N^G$-nitroarginine methy ester. When rhRLX-impregnated Matrigel pellets were implanted in mice, vascularization and incorporation of GFP-labeled BMDEC were stimulated.

In BMDEC isolated from relaxin/insulin-like family peptide receptor (Rxfp2) and wild-type, but not Rxfp1 knock-out mice, rhRLX also rapidly increases NO production. Similarly, rhRLX increases circulating BMDEC number in Rxfp2 and wild-type, but not Rxfp1 knock-out mice as assessed by colony formation and flow cytometry. Taken together, these results indictate that relaxin effects BMDEC function through the Rxfp1 receptor.

Relaxin is advantageous compared to other agents (e.g., GM-CSF, EPO, VEGF)' in providing therapy because it does not induce a proinflammatory effect and may be anti-inflammatory. In addition, relaxin has other beneficial actions including vasodilation and increasing arterial compliance.

The subject invention provides methods for increasing BMDEC number and function (e.g., BMDEC migration and circulation) in a subject. In a related embodiment, the invention provides methods for promoting angiogenesis and/or vasculogenesis, neovascularization and vascular remodeling. In another related embodiment, the subject invention provides methods for stimulating NO production, particularly NO in CD34+ BMDEC.

The subject invention is applicable to a variety of different organisms, including, for example, mammals. In a preferred embodiment, the subject is a human. Although medical applications with humans are clearly foreseen, veterinary applications are also envisaged.

Therapeutic Applications

The terms "treatment," "treating," "therapy," and the like are used herein to generally refer to obtaining a desired therapeutic, pharmacologic or physiologic effect. The effect may be therapeutic in terms of a partial or complete cure for a disease and/or partially or completely relieving an adverse effect/symptom attributable to the disease.

In addition, the subject invention may also prevent the disease from occurring in a subject who may be predisposed to the disease but has not yet been diagnosed as having it; or inhibit the disease, i.e., arresting its development.

According to the subject invention, relaxin can be used for bone or other tissue repair where improved blood supply is needed. For example, relaxin can be used in accordance with the subject invention to assist in bone or tissue growth or regeneration (such as from a bone fracture or bone surgery) by increasing BMDEC number and activity to induce angiogenesis and/or vasculogenesis, as well as for wound healing and tissue repair, and in the treatment of burns, incisions and ulcers. In a related embodiment, relaxin can be used in accordance with the subject invention to assist in treating osteoporosis.

According to the subject invention, relaxin may be used for improving blood supply to organs or tissues that require such. For example, relaxin can be used in treating diseases associated with vasoconstriction, such as glaucoma, chronic stable angina; unstable angina; vasospastic angina; microvascular angina, heart failure, migraine, pulmonary hypertension; renal hypertension; essential hypertension; atheroembolic diseases; renal vein thrombosis; and renal artery stenosis.

In addition, relaxin can be used in treating diseases characterized or caused by insufficient angiogenesis or vessel regression. For example, relaxin can be used in accordance with the subject invention to treat, without limitation, pancreatic islet cell injury and nephropathy as well as glomerulosclerosis and tubulointerstial fibrosis that are characterized by vessel dropout, microvasculopathy and endothelial cell dysfunction; gastric or oral ulcerations (where delayed healing occurs due to production of angiogenesis inhibitors by pathogens) and Crohn's disease (which is characterized by mucosal ischemia); hair loss (or retarded hair growth) by angiogenesis inhibitors as well as skin purpura, telangiectasia, and venous lake formation due to age-dependent reduction of vessel number and maturation; systemic sclerosis and Lupus due to insufficient angiogenic response.

According to the subject invention, relaxin can also be used for inducing blood flow to nerve and brain tissue, e.g. for the treatment of central and peripheral nervous system diseases and neuropathies, as well as mechanical and traumatic disorders, which involve reduced blood flow to neural cells or nerve tissue. More specifically, relaxin may be used in the treatment of Alzheimer's and Parkinson's disease as well as amyotrophic lateral sclerosis and diabetic neuropathy. Further conditions that may be treated in accordance with the invention include mechanical and traumatic disorders, such as trauma and cerebrovascular diseases such as stroke. Peripheral neuropathies resulting from decreased blood flow as a result of chemotherapy or other medical therapies can also be treated using relaxin.

Relaxin, by mobilizing BMDEC and enhancing BMDEC integration into various sites can also be used for improving organ function following transplantation (e.g., heart, pancreas, liver, intestine, kidney, skin, endothelium). In addition, relaxin may be used to improve the vascularization of skin grafts or reattached limbs so as to preserve their function and viability and/or to improve the healing of surgical anastomoses (e.g., reconnecting sections of the bowel after gastrointestinal surgery).

According to the subject invention, relaxin can be used in preserving the function and long-term patency of dialysis access. A hemodialysis access (or vascular access) is a large diameter, fast flowing conduit (such as a catheter, graft or fistula) that is located just beneath the skin surface. Preserving access function and long-term patency are essential for efficient dialysis delivery. Unfortunately, maintenance of a reliable hemodialysis access to the circulation has been an Achilles' heel of modern haemodialysis. By mobilizing BMDEC and enhancing BMDEC integration into appropriate sites, the subject invention provides a solution to the current problems associated with dialysis access.

The subject invention also provides methods for treating various forms of ischemia (including mesenteric or limb ischemia). According to one embodiment of the invention, a method for treating uteroplacental ischemia, including preeclampsia, is provided via the administration of relaxin to induce BMDEC migration and numbers. In preeclampsia, there is a failure of endothelial cells to re-grow and cover the uteroplacental arteries near term. This may contribute to spasm of these arteries in preeclampsia (and in severe intrauterine growth restriction). Inadequate remodeling of uterine artery and smaller branches may be a factor in uteroplacental ischemia.

According to the subject invention, relaxin can be administered to a subject to decrease vascular resistance and increase global arterial compliance. By mobilizing BMDEC and enhancing BMDEC integration into appropriate sites, relaxin can promote vasculogenesis (as well as arterial remodeling), in maternal organs such as the uterus, pancreas and breast to encourage healthy pregnancy.

In a related embodiment, the invention provides a method for improving placentation in a mother. Relaxin can be administered to a pregnant subject to mobilize BMDEC and enhance BMDEC integration, thereby promoting optimal remodeling of the uterine artery and smaller branches, and by increasing the number of blood vessels in the endometrium.

Insofar as recurrent spontaneous abortion has a vascular component, the subject invention provides a method for promoting successful pregnancy and/or birth outcomes. Relaxin may be administered to a subject to improve endometrial vasculogenesis via incorporation of more BMDEC. In a related embodiment, relaxin can be administered to a subject to improve fetal implantation in a subject. As described herein, relaxin induces BMDEC migration and number and function. The administration of relaxin can improve implantation by increasing the number of blood vessels in the endometrium of a subject.

In another embodiment, relaxin is administered to a pregnant subject to treat fetoplacental ischemia. Fetoplacental ischemia results in failure of adequate fetal growth during pregnancy.

In another embodiment, relaxin is administered to a pregnant subject to improve fetal growth and development. In particular, relaxin is administered to a pregnant subject to promote and improve fetoplacental and fetal vasculature. By increasing maternal circulating BMDEC number and activity, which may traffic to fetoplacental vasculature and to the fetal vasculature, the subject invention can improve fetoplacental blood flow and fetal growth. For example, increased numbers of maternal BMDEC may become permanently engrafted in the fetal vasculature, thereby improving endothelial dilation and function and increasing arterial compliance during fetal and neonatal life, as well as during early development and adulthood. Thus, this treatment method can be a mechanism for combating poor fetal growth and developmental origins of disease (e.g., reducing coronary heart disease and other cardiovascular complications in adulthood associated with being pathologically small in utero, and treatment of neonatal respiratory distress syndrome that is associated with insufficient lung maturation due to insufficient angiogenesis).

According to the subject invention, relaxin can also be used in facilitating adaptation to high altitude or otherwise low oxygen environments.

According to the subject invention, relaxin can also be used in improving skeletal muscle angiogenesis and/or vasculogenesis and blood flow in athletes or those suffering from conditions with reduced blood flow (e.g., muscular dystrophy).

In one embodiment of the invention, methods are provided for blocking the activity of relaxin. For example, in one embodiment, an antagonist of relaxin can be used in accordance with the subject invention to treat menorrhagia (uterine bleeding). In another embodiment, methods are provided that enable inhibition of BMDEC migration and/or NO production and are useful in treating conditions amenable to treatment by inhibiting BMDEC and/or local vasculogenesis and/or increased blood flow. For example, the subject invention provides methods for treating diseases characterized or caused by abnormal or excessive vasculogenesis by blocking the activity of relaxin, for example blocking relaxin's activity at the Rxfp1 receptor. These conditions include, without limitation, cancer (such as prostate cancer); vasculitis in autoimmune disorders such as systemic sclerosis, multiple sclerosis, and Sjögren's disease; vascular malformations such as those in Tie-2 mutation; DiGeorge syndrome; hereditary hemorrhagic telangiectasia; cavernous hemangioma; cutaneous hemangioma; persistent hyperplastic vitreous syndrome; diabetic retinopathy; age-related macular degeneration and retinopathy of prematurity; choroidal neovascularization; primary pulmonary hypertension; asthma, nasal polyps; rhinitis; chronic airway inflammation; cystic fibrosis; inflammatory bowel disease (ulcerative colitis) and periodontal disease; ascites; peritoneal adhesions; liver cirrhosis; endometriosis; uterine bleeding; ovarian cysts; ovarian hyperstimulation; rheumatoid arthritis; osteomyelitis; ostophyte formation; warts; allergic dermatitis; scar keloids; pyogenic granulomas; blistering disease; Kaposi's sarcoma in AIDS patients; diabetic nephropathy; and psoriasis.

Relaxin, Relaxin Analogs, Agonists and Antagonists

In various embodiments, the subject invention pertains to relaxin as well as agonists, analogs, derivatives, small molecule relaxin effector, small molecule/non-peptide mimetic of relaxin, and conjugates of relaxin, which have the ability to regulate BMDEC number and function as well as stimulate NO production. In other embodiments of the invention, relaxin antagonists are provided for use in modulating BMDEC mobilization and integration and/or reducing and/or inhibiting vasculogenesis.

Relaxin has been well defined in its natural human form, animal form, and in its synthetic form. In particular, relaxin has been described in U.S. Pat. Nos. 5,166,191 and 4,835,251 (both of which are hereby incorporated by reference). In accordance with the subject invention, "relaxin" generally refers to the terms "relaxin," "human relaxin," "native relaxin," and "synthetic relaxin" as defined in U.S. Pat. No. 5,166,191 and the terms "human relaxin" and "human relaxin analogs" are as defined in U.S. Pat. No. 4,835,251.

In one embodiment, the relaxin is human relaxin, as described in, for example, U.S. Pat. Nos. 5,179,195; 5,023,321; and 4,758,516 (the disclosures of which are incorporated by reference herein). Relaxin can also be isolated from pigs, rats, horses, and other mammals. Relaxin can also be produced by recombinant techniques.

Methods of making relaxin and its analogs are known in the art. In addition, methods for isolating and purifying relaxin are known in the art. Several sources for these methods are identified in U.S. Pat. No. 5,166,191, including the following references: U.S. Pat. No. 4,835,251, Barany et al., The Peptides 2:1 (1980), Treager et al., Biology of Relaxin and its Role in the Human, pp. 42-55; EP 0 251 615; EP 0 107 782; EP 0 107 045; and WO 90/13659 (all of which are incorporated by reference herein).

Additional methods of making relaxin are described in U.S. Pat. No. 5,464,756, and PCT/US94/06997 (the disclosures of which are incorporated by reference herein). Relaxin can also be prepared by synthesis of the A and B chains, and purification and assembly thereof, as described in European Patent 0 251 615 published Jan. 7, 1988, the disclosure of which is incorporated herein by reference). For in vitro assembly of relaxin, a 4:1 molar ratio of A to B chains is generally employed. The resulting product is then purified by any means known to one of ordinary skill in the art, including, for example, reverse-phase HPLC, ion exchange chromatography, gel filtration, dialysis, and the like, or any combination of such procedures. Unprocessed or partially processed forms of relaxin, such as preprorelaxin or prorelaxin, can also be used.

In specific embodiments, relaxin polypeptides include the H1 and H2 forms of human relaxin. It has been reported that the predominant species of human relaxin is the H2 relaxin form with a truncated B chain (i.e., relaxin H2(B29 A24)), wherein the four C-terminal amino acids of the B-chain are absent so that the B-chain ends with a serine at position 29. Either this form (referred to as "short relaxin" or "long relaxin" which contains a B chain of 33 amino acids) can be used.

Relaxin agonists include analogs, such as naturally-occurring amino acid sequence variants of relaxin. Relaxin analogs also include those altered by substitution, addition or deletion of one or more amino acid residues that provide for functionally active relaxin polypeptides. Such relaxin analogs include, but are not limited to, those containing as a primary amino acid sequence all or part of the amino acid sequence of a relaxin polypeptide, including altered sequences in which one or more functionally equivalent amino acid residues are substituted for residues within the sequence, resulting in a silent functional change (e.g., a conservative substitution), wherein the relaxin agonist retains the biological activity of relaxin as described herein.

In another aspect, the relaxin agonist is a polypeptide consisting of, or comprising, a fragment of a relaxin polypeptide having at least 10 contiguous amino acids of the relaxin polypeptide. Alternatively, the fragment contains at least 20 or 25 contiguous amino acids of the relaxin polypeptide. In other embodiments, the fragments are not larger than 20 or 30 amino acids.

The relaxin analog can be a polypeptide comprising regions that are substantially similar to a relaxin polypeptide or fragments thereof (e.g., in various embodiments, at least 60%, 70%, 75%, 80%, 90%, or even 95% identity over an amino acid sequence of identical size), or when compared to an aligned sequence in which the alignment is done by a computer sequence comparison/alignment program known in the art, or which coding nucleic acid is capable of hybridizing to a relaxin nucleic acid, under high stringency conditions. (See, e.g., Smith and Waterman, Adv. Appl Math. 2:482 (1981); Needleman and Wunsch, J. Mol. Biol. 48:443 (1970); Pearson and Lipman, Proc. Natl. Acad. Sci. USA 85:2444 (1988); GAP, BESTFIT, FASTA, and TEASTA in the Wisconsin Genetics Software Package, Genetics Computer Group, 575 Science Dr., Madison, Wis.); Ausubel et al. (eds.), Current Protocols in Molecular Biology, 4th ed., John Wiley and Sons, New York (1999); the disclosures of which are incorporated by reference herein). Relaxin agonists further comprise functionally active relaxin polypeptides, analogs or fragments that bind to a relaxin receptor and retain the biological activity described herein.

Relaxin agonists, such as relaxin polypeptides, analogs and fragments can be produced by various methods known in the art. The manipulations that result in their production can occur at the gene or polypeptide level. For example, cloned relaxin nucleic acids can be modified by any of numerous strategies known in the art (see, e.g., Sambrook et al., Molecular Cloning: A Laboratory Manual, 3d Ed., Cold Spring Harbor Laboratory Press, New York (2001); Ausubel et al., Current Protocols in Molecular Biology, 4th ed., John Wiley and Sons, New York (1999); which are incorporated by reference herein), such as making conservative substitutions, deletions, insertions, and the like. The sequence can be cleaved at appropriate sites with restriction endonuclease(s), followed by further enzymatic modification if desired, isolated, and ligated in vitro. In the production of the relaxin nucleic acids encoding an analog or fragment, the modified nucleic acid typically remains in the proper translational reading frame, so that the reading frame is not interrupted by translational stop signals or other signals that interfere with the synthesis of the relaxin analog or fragment. The relaxin nucleic acid can also be mutated in vitro or in vivo to create and/or destroy translation initiation and/or termination sequences. The relaxin nucleic acid can also be mutated to create variations in coding regions and/or to form new restriction endonuclease sites or destroy preexisting ones and to facilitate further in vitro modification. Any technique for mutagenesis known in the art can be used, including but not limited to, chemical mutagenesis, in vitro site-directed mutagenesis (see, e.g., Hutchison et al., J. Biol. Chem. 253:6551-60 (1978)), the use of TAB® linkers (Pharmacia), and the like. (See generally Sambrook et al., supra; Ausubel et al., supra.).

In a specific embodiment, relaxin analogs are prepared from relaxin-encoding nucleic acids that are altered to introduce aspartic acid codons at specific position(s) within at least a portion of the relaxin coding region. (See, e.g., U.S. Pat. No. 5,945,402, the disclosure of which is incorporated by reference herein.) The resulting analogs can be treated with dilute acid to release a desired analog, thereby rendering the protein more readily isolated and purified. Other relaxin analogs are disclosed in U.S. Pat. Nos. 4,656,249; 5,179,195; 5,945,402; 5,811,395; and 5,795,807 (the disclosures of which are incorporated by reference herein).

Manipulations of the relaxin polypeptide sequence can also be made at the polypeptide level. Included within the scope of the invention are relaxin polypeptides, analogs or fragments that are differentially modified during or after synthesis (e.g., in vivo or by in vitro translation). Such modifications include conservative substitution, glycosylation, acetylation, phosphorylation, amidation, derivatization by known protecting/blocking groups, proteolytic cleavage, linkage to an antibody molecule, another polypeptide or other cellular ligand, and the like. Any of numerous chemical modifications can be carried out by known techniques, including, but not limited to, specific chemical cleavage (e.g., by cyanogen bromide), enzymatic cleavage (e.g., by trypsin; chymotrypsin, papain, V8 protease, and the like); modification by, for example, $NaBH_4$, acetylation, formylation, oxidation and reduction, metabolic synthesis in the presence of tunicamycin, and the like.

Relaxin polypeptides, analogs and fragments can be purified from natural sources by standard methods such as those described herein (e.g., immunoaffinity purification). Relaxin polypeptides, analogs and fragments can also be isolated and purified by standard methods including chromatography (e.g., ion exchange, affinity, sizing column chromatography, high pressure liquid chromatography), centrifugation, differential solubility, or by any other standard technique for the purification of polypeptides. Relaxin polypeptides can be synthesized by standard chemical methods known in the art (see, e.g. Hunkapiller et al., Nature 310:105-11 (1984); Stewart and Young, Solid Phase Peptide Synthesis, $2^{nd}$ Ed., Pierce Chemical Co., Rockford, Ill., (1984); the disclosures of which are incorporated by reference herein).

In addition, analogs of relaxin polypeptides can be chemically synthesized. For example, a peptide corresponding to a fragment of a relaxin polypeptide, which comprises a desired domain, or which mediates a desired activity in vivo, can be synthesized by use of chemical synthetic methods using, for example, an automated peptide synthesizer. Furthermore, if desired, nonclassical amino acids or chemical amino acid analogs can be introduced as a substitution or addition into the relaxin polypeptide sequence. Non-classical amino acids include, but are not limited to, the D-isomers of the common amino acids, α-amino isobutyric acid, 4-aminobutyric acid, 2-amino butyric acid, 8-amino hexanoic acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or t (levorotary).

In another embodiment, the relaxin agonist is a chimeric, or fusion, protein comprising a relaxin polypeptide, or fragment thereof (typically consisting of at least a domain or motif of the relaxin polypeptide, or at least 10 contiguous amino acids of the relaxin polypeptide), joined at its amino- or carboxy-terminus via a peptide bond to an amino acid sequence of a different protein. In one embodiment, such a chimeric protein is produced by recombinant expression of a nucleic acid encoding the chimeric polypeptide. The chimeric product can be made by ligating the appropriate nucleic acid sequences, encoding the desired amino acid sequences, to each other in the proper reading frame and expressing the chimeric product by methods commonly known in the art. Alternatively, the chimeric product can be made by protein synthetic techniques (e.g., by use of an automated peptide synthesizer).

In a specific embodiment, the fusion protein is a relaxin-ubiquitin fusion protein. For example, U.S. Pat. No. 5,108,919 (the disclosure of which is incorporated herein by reference) discloses methods for preparing a fusion protein of a relaxin chain and ubiquitin.

The subject invention specifically provides methods for stimulating BMDEC mobilization via administration to a subject an effective amount of relaxin, a relaxin analog, a relaxin agonist, a small molecule relaxin effector, a small molecule/non-peptide mimetic of relaxin, a relaxin nucleic acid, and the like.

In preferred embodiments, the relaxin analog, relaxin agonist, small molecule relaxin effector, small molecule/non-peptide mimetic of relaxin, relaxin nucleic acid, or relaxin fragment is functionally active (i.e., capable of exhibiting one or more functional activities associated with a full-length, wild-type relaxin polypeptide as described herein). As one example, analogs or fragments that retain a desired relaxin property of interest (e.g., binding to a relaxin receptor to stimulate NO production in BMDEC or activating DMDEC mobilize and integrate in sites for vasculogenesis) can be used as inducers of such property and its physiological correlates. Specific embodiments of the invention relate to the use of a relaxin analog or fragment in treating conditions amenable to treatment by recruitment of BMDEC. Analogs or fragments of relaxin can be tested for the desired activity by procedures known in the art, including but not limited to the functional assays described herein.

In another aspect of the invention, compounds that block relaxin activity are provided for modulating BMDEC mobilization and integration, and/or vasculogenesis. Compounds that block relaxin activity include relaxin antagonists. Relaxin antagonists include, for example, relaxin binding agents, relaxin receptor binding agents, small molecule relaxin antagonist, antisense nucleic acids, and the like.

Relaxin antagonists can also be antibodies that immunospecifically-recognize relaxin or a relaxin receptor polypeptide and that reduce or inhibit relaxin-associated activity (such as inducing BMDEC mobilization and integration and/or NO production) in cell populations or tissues. Antirelaxin and anti-relaxin receptor antibodies include, but are not limited to, polyclonal antibodies, monoclonal antibodies, chimeric antibodies (e.g., fully humanized antibodies or human chimeric antibodies), single chain antibodies, antibody fragments (e.g., Fab, F(ab'), F(ab')$_2$, Fv, or hypervariable regions), single heavy chains, and an Fab expression library. In a specific embodiment, polyclonal and/or monoclonal antibodies to full length, vertebrate or mammalian relaxin or relaxin receptor polypeptide are produced and selected for those antibodies that selectively bind to relaxin or a relaxin receptor polypeptide, and thereby functionally inactivate such polypeptides. In another embodiment, antibodies to a domain of a vertebrate relaxin polypeptide, or a relaxin receptor polypeptide, are produced.

Various procedures known in the art can be used for the production of polyclonal antibodies to a relaxin or relaxin receptor polypeptide, or a fragment or analog thereof. For the production of such antibodies, various host animals (including, but not limited to, rabbits, mice, rats, sheep, goats, and the like) can be immunized by injection with the native relaxin or relaxin receptor polypeptide, or a fragment or analog thereof.

For preparation of monoclonal antibodies directed toward a relaxin or relaxin receptor polypeptide, fragment, or analog thereof, any technique which provides for the production of antibody molecules by continuous cell lines in culture can be used. Such techniques include, for example, the hybridoma technique originally developed by Kohler and Milstein (Nature 256:495-97 (1975)), as well as the trioma technique, the human B-cell hybridoma technique (see, e.g., Kozbor et al., Immunology Today 4:72 (1983)), and the EBV-hybridoma technique to produce human monoclonal antibodies (see, e.g., Cole et al, In Monoclonal Antibodies and Cancer Therapy, Alan R. Liss, Inc., pp. 77-96 (1985)).

Further to the invention, "chimeric" or "humanized" antibodies (see, e.g., Morrison et al., Proc. Natl. Acad. Sci. USA 81:6851-55 (1984); Neuberger et al, Nature 312:604-08 (1984); Takeda et al., Nature 314:452-54 (1985)) can be prepared. Such chimeric antibodies are typically prepared by splicing the non-human genes for an antibody molecule specific for a relaxin or receptor polypeptide together with genes from a human antibody molecule of appropriate activity. It can be desirable to transfer the antigen binding regions (e.g., an F(ab')$_2$, F(ab'), Fv, or hypervariable region (s)) of non-human antibodies into the framework of a human antibody by recombinant DNA techniques to produce a substantially human molecule. In a preferred embodiment, the antibodies are fully humanized.

Methods for producing such "chimeric" molecules are generally well known and described in, for example, U.S. Pat. Nos. 4,816,567; 4,816,397; 5,693,762; 5,712,120; 5,821,337; 6,054,297; International Patent Publications WO 87/02671 and WO 90/00616; and European Patent Publication EP 0 239 400 (the disclosures of which are incorporated by reference herein).

In another aspect of the invention, the relaxin antagonist is a relaxin binding agent comprising a soluble relaxin receptor, or a fragment or analog thereof, that binds relaxin. The term "soluble relaxin receptor" refers to a relaxin receptor polypeptide that is not bound to a cell membrane. The relaxin receptor is approximately 200 kilodaltons. (See Palejwala et al., Endocrinology 139(3):1208-12 (1998), the disclosure of which is incorporated by reference herein.) The soluble form of the relaxin receptor retains the ability to bind vertebrate relaxin, but typically lacks transmembrane and/or cytoplasmic domains. Soluble relaxin receptors can comprise additional amino acid residues, such as affinity tags, that provide for a means for purification of the polypeptide or to provide sites for attachment of the polypeptide to another polypeptide, or to immunoglobulin sequences.

The relaxin antagonist can further be a relaxin analog, such as a relaxin polypeptide that binds to a relaxin receptor but fails to induce a response by that receptor. For example, the relaxin analog can be a competitive inhibitor of relaxin binding or a conventional antagonist of the relaxin receptor Rxfp1. Methods of making such analogs are known in the art (supra). Such relaxin analogs can be prepared by modification of relaxin polypeptides such that the relaxin analog retains relaxin receptor binding activity, but does not induce a response by the relaxin receptor. For example, relaxin analogs can be amino acid sequence variants of relaxin that retain relaxin receptor Rxfp1 binding activity, but that fail to induce a response by a relaxin receptor Rxfp1. Relaxin analogs further include relaxin polypeptides, altered by addition or deletion of one or more amino acid residues, that retain receptor-binding function but fail to induce a response by relaxin receptor.

The relaxin (antagonist) analog can be a polypeptide comprising regions that are substantially similar to a relaxin polypeptide (e.g., in various embodiments, at least 60%, 70%, 75%, 80%, 90%, or even 95% identity or similarity over an amino acid sequence of identical size), or when compared to an aligned sequence in which the alignment is done by a computer sequence comparison/alignment program known in the art, or which coding nucleic acid is capable of hybridizing to a relaxin nucleic acid, under high stringency, moderate stringency, or low stringency conditions.

In another embodiment, the relaxin (antagonist) analog is a chimeric, or fusion, protein comprising a relaxin polypeptide (typically consisting of at least a domain or motif of the relaxin polypeptide, or at least 10 contiguous amino acids of the relaxin polypeptide) joined at its amino- or carboxy-terminus via a peptide bond to an amino acid sequence of a different protein. In one embodiment, such a chimeric protein is produced by recombinant expression of a nucleic acid encoding the chimeric polypeptide.

Functional Assays

The activity of relaxin agonists and antagonists, and of relaxin receptor agonists and antagonists, can be determined by standard assays for relaxin and/or relaxin receptor activity. For example, one standard functional assay is the measurement of cAMP in THP-1 cells.

In one aspect of the invention, the activity of a relaxin agonist is assayed. For example, the ability of a relaxin agonist to activate BMDEC migration is assayed. In another aspect of the invention, the ability of a relaxin antagonist to inhibit relaxin functional activity by binding to relaxin is assayed. Similarly, the ability of a relaxin antagonist to inhibit relaxin function, or relaxin receptor function, can be assayed by, for example, adding a relaxin antagonist to a relaxin receptor assay and determining the inhibition, as compared with a control without the relaxin antagonist. Suitable measurements of relaxin antagonist activity include measuring percent inhibition, $IC_{50}$, and the like.

Suitable assays for measuring relaxin or relaxin receptor agonist or antagonist activity, include, for example, those described in the following references (which are incorporated by reference herein): MacLennan et al., Ripening of the Human Cervix and Induction of Labor with Intracervical Purified Porcine Relaxin, Obstetrics & Gynecology 68:598-601 (1986); Poisner et al., Relaxin Stimulates the Synthesis and Release of Prorenin From Human Decidual Cells: Evidence For Autocrine/Paracrine Regulation, J. Clinical Endocrinology and Metabolism 70:1765-67 (1990); O'Day-Bowman et al, Hormonal Control of the Cervix in Pregnant Gilts. III. Relaxin's Influence on Cervical Biochemical Properties in Ovariectomized Hormone-Treated Pregnant Gilts, Endocrinology 129:1967-76 (1991); Saugstad, Persistent Pelvic Pain and Pelvis Joint Instability, Eur. J. Obstetrics & Gynecology and Reproductive Biology 41:197-201 (1991).

Other assays include those disclosed by Buliesbach et al., The Receptor-Binding Sites of Human Relaxin II, J. Biol. Chem. 267:22957-60 (1992); Hall et al., Influence of Ovarian Steroids on Relaxin-Induced Uterine Growth in Ovariectomized Gilts, Endocrinology 130:3159-66 (1992); Kibblewhite et al., The Effect of Relaxin on Tissue Expansion, Arch. Otolaryngol. Head Neck Surg. 118:153-56 (1992); Lee et al., Monoclonal Antibodies Specific for Rat Relaxin. VI. Passive Immunization with Monoclonal Antibodies Throughout the Second Half of Pregnancy Disrupts Histological Changes Associated with Cervical Softening at Parturtion in Rats, Endocrinology 130:2386-91 (1992); Bell et al., A Randomized, Double-Blind Placebo-Controlled Trial of the Safety of Vaginal Recombinant Human Relaxin for Cervical Ripening, Obstetrics & Gynecology 82:328-33 (1993); Bryant-Greenwood et al., Sequential Appearance of Relaxin, Prolactin and IGFBP-1 During Growth and Differentiation of the Human Endometrium, Molecular and Cellular Endocrinology 95:23-29 (1993); Chen et al., The Pharmacokinetics of Recombinant Human Relaxin in Nonpregnant Women After Intravenous, Intravaginal, and Intracervical Administration, Pharmaceutical Research 10:834-38 (1993); Huang et al., Stimulation of Collagen Secretion by Relaxin and Effect of Oestrogen on Relaxin Binding in Uterine Cervical Cells of Pigs, Journal of Reproduction and Fertility 98:153-58 (1993).

Additional assays are disclosed in Saxena et al., Is the Relaxin System a Target for Drug Development? Cardiac Effects of Relaxin, TiPS 14:231 (June 1993, letter); Winn et al, Hormonal Control of the Cervix in Pregnant Gilts. IV. Relaxin Promotes Changes in the Histological Characteristics of the Cervix that are Associated with Cervical Softening During Late Pregnancy in Gilts, Endocrinology 133: 121-28 (1993); Colon et al., Relaxin Secretion into Human Semen Independent of Gonadotropin Stimulation, Biology of Reproduction 50:187-92 (1994); Golub et al., Effect of Short-Term Infusion of Recombinant Human Relaxin on Blood Pressure in the Late-Pregnant Rhesus Macaque (*Macaca Mulatta*), Obstetrics & Gynecology 83:85-88 (1994); Jauniaux et al., The Role of Relaxin in the Development of the Uteroplacental Circulation in Early Pregnancy, Obstetrics & Gynecology 84:338-342 (1994); Johnson et al., The Regulation of Plasma Relaxin Levels During Human Pregnancy, J. Endocrinology 142:261-65 (1994); Lane et al., Decidualization of Human Endometrial Stromal Cells in Vitro: Effects of Progestin and Relaxin on the Ultrastructure and Production of Decidual Secretory Proteins, Human Reproduction 9:259-66 (1994); Lanzafame et al., Pharmacological Stimulation of Sperm Motility, Human Reproduction 9:192-99 (1994); Petersen et al., Normal Serum Relaxin in Women with Disabling Pelvic Pain During Pregnancy, Gynecol. Obstet. Invest. 38:21-23 (1994); Tashima et al., Human Relaxins in Normal, Benign and Neoplastic Breast Tissue, J. Mol. Endocrinology 12:351-64 (1994); Winn et al. Individual and Combined Effects of Relaxin, Estrogen, and Progesterone in Ovariectomized Gilts. I. Effects on the Growth, Softening, and Histological Properties of the Cervix, Endocrinology 135:1241-49 (1994); Winn et al., Individual and Combined Effects of Relaxin, Estrogen, and Progesterone on Ovariectomized Gilts. II. Effects on Mammary Development, Endocrinology 135:1250-55 (1994); Bryant-Greenwood et al., Human Relaxins: Chemistry and Biology, Endocrine Reviews 15:5-26 (1994); Johnson et al., Relationship Between Ovarian Steroids, Gonadotrophins and Relaxin During the Menstrual Cycle, Acta Endocrinilogica 129:121-25 (1993).

In yet another aspect of the invention, the activity of an agonist or antagonist is determined by measuring the ability of the agonist or antagonist to compete with wild-type relaxin polypeptide, or relaxin receptor polypeptide, for binding to anti-relaxin antibody. Various immunoassays known in the art can be used. Such assays include, but are not limited to, competitive and non-competitive assay systems using techniques such as radioimmunoassays, ELISA (enzyme linked immunosorbent assay) "sandwich" immunoassays, immunoradiometric assays, gel diffusion precipitin reactions, immunodiffusion assays, in situ immunoassays (using colloidal gold, enzyme or radioisotope labels, and the like), Western blots, precipitation reactions, agglutination assays (e.g., gel agglutination assays or hemagglutination assays), complement fixation assays, immunofluorescence assays, protein A assays, immunoelectrophoresis assays, and the like. Antibody binding can be detected by measuring the amount of label on the primary antibody that is bound, or prevented from binding to, a substrate. Alternatively, primary antibody binding is detected by measuring binding of a secondary antibody or reagent to the primary antibody. The secondary antibody can also be directly labeled. Many means are known in the art for detecting binding in an immunoassay and are considered within the scope of the present invention.

The functional activity of an agonist or antagonist can also be determined in an in vivo system. For example, the ability of relaxin agonists or antagonists to modulate NO production and/or BMDEC migration in a cell population and/or tissues can be measured. The assays described above can be used to determine the activity resulting from expression of relaxin agonists or antagonists in vertebrate cells. Alternatively, relaxin agonist or antagonist can be expressed in a heterologous system and the activity of the relaxin agonist or antagonist can be assayed as a modulator of a physiological change in that system (for example, the ability to modulate BMDEC mobilization and/or vasculogenesis in vertebrate tissues).

Routes of Administration

The invention provides methods for the administration to a subject of an effective amount of relaxin (such as human relaxin, a relaxin agonist or analog, etc.), also referred to collectively as an "active agent." Typically, the active agent is substantially purified prior to formulation.

According to the subject invention, an "effective amount" means a dosage sufficient to provide treatment for the disease state being treated. This will vary depending on the subject, the disease and the treatment being effected. The amount (e.g., relaxin or an antagonist of relaxin) administered will, of course, be dependent on the size, sex and weight of the subject and the severity of the disease or condition, the manner and schedule of administration, the likelihood of recurrence of the disease, and the judgment of the prescribing physician.

Various delivery systems are known and can be used to administer an active agent, such as, for example, by infusion, injection (e.g., intradermal, intramuscular or intraperitoneal), oral delivery, nasal-delivery, intrapulmonary delivery, rectal delivery, transdermal delivery, interstitial delivery or subcutaneous delivery. In a specific embodiment, it can be desirable to administer the active agent locally to the area in need of treatment; this administration can be achieved by, for example, and not by way of limitation, local infusion, topical application, by injection (e.g., intratesticular or intraprostatic), by means of a catheter, or by means of an implant, the implant being for example, a porous, non-porous, gelatinous or polymeric material, including membranes such as silastic membranes or fibers. In one embodiment, administration can be by direct injection at the target site.

Pharmaceutical compositions containing the active agent can be formulated according to the desired delivery system. Such pharmaceutical compositions typically comprise a therapeutically effective amount of active agent and a pharmaceutically acceptable carrier. The term "pharmaceutically acceptable" means approved by a regulatory agency of the Federal or a state government or listed in the U.S. Pharmacopeia or other generally recognized pharmacopeia for use in vertebrates, typically animals, and more typically in humans. The term "carrier" refers to a diluent, adjuvant, excipient, stabilizer, preservative, viscogen, or vehicle with which the active agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Suitable excipients include starch, glucose, lactose, sucrose, gelatin, malt, rice, flour, chalk, silica gel, sodium stearate, glycerol monostearate, talc, sodium chloride, dried skim milk, glycerol, propylene glycol, ethanol, and the like. The composition, if desired, can also contain minor amounts of wetting or emulsifying agents, or pH buffering agents.

Suitable preservatives include, for example, sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, potassium benzoate, potassium metabisulfite, potassium sorbate, sodium bisulfite, sulfur dioxide, organic mercurial salts, phenol and ascorbic acid. Suitable viscogens include, for example, carboxymethylcellulose, sorbitol, dextrose, and polyethylene glycols. Other examples of suitable pharmaceutical carriers are described in, for example, Remington's Pharmaceutical Sciences (Gennaro (ed.), Mack Publishing Co., Easton, Pa. (1990)).

The active agent can also be formulated as a neutral or salt form. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

In one embodiment, the active agent is formulated in accordance with routine procedures as a pharmaceutical composition adapted for intravenous administration. For intravenous delivery, water is a typical carrier. Saline, aqueous dextrose and glycerol solutions can also be employed as liquid carriers, particularly for injectable solutions. Typically, compositions for intravenous administration are solutions in sterile isotonic aqueous buffer. Where necessary, the composition can also include a solubilizing agent and a local anesthetic to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Orally deliverable compositions can take the form of solutions, suspensions, emulsions, tablets, pills, capsules, powders, sustained-release formulations, and the like. Oral formulations can include standard carriers such as pharmaceutical grades of mannitol, lactose, starch, magnesium stearate, sodium saccharine, cellulose, magnesium carbonate, and the like.

For rectal administration, the compositions are formulated according to standard pharmaceutical procedures. Typically, the composition is formed as a meltable composition, such as a suppository. Suppositories can contain adjuvants which provide the desired consistency to the composition.

Nasal administration is typically performed using a solution as a nasal spray and can be dispensed by a variety of methods known to those skilled in the art. Systems for intranasally dispensing liquids as a spray are well known (see, e.g., U.S. Pat. No. 4,511,069, which is incorporated by reference herein). Preferred nasal spray solutions comprise the active agent in a liquid carrier that optionally includes a nonionic surfactant for enhancing absorption of the drug and one or more buffers or other additives to minimize nasal irritation. In some embodiments, the nasal spray solution further comprises a propellant. The pH of the nasal spray solution is typically between about pH 6.8 and 7.2.

Intrapulmonary dosage forms containing the active agent can be administered to the respiratory tract intranasally or by breathing a spray or aerosol containing the active agent. The active agent is typically delivered directly into the lungs in a small particle aerosol, which is specifically targeted to the smallest air passages and alveoli.

The particulate aerosol suspensions are typically fine dry powders containing the active agent. Particulate aerosol suspension are prepared by any number of conventional procedures. The simplest method of preparing such suspensions is to micronize the active agent (e.g., as crystals or lyophilization cakes), and suspend the particles in dry fluorocarbon propellants. In these formulations the active agent is preferably suspended in the fluorocarbon. In an alternate embodiment, the active agent is stored in a compartment separate from the propellant. Discharge of the propellant withdraws a predetermined dose from the storage compartment. The devices used to deliver active agents in this manner are known as metered dose inhalers (MDIs) (see, e.g., Byron, Drug Development and Industrial Pharmacy 12:993 (1986), which is incorporated by reference herein).

The amount of the active agent which will be effective in the treatment of a particular subject will depend on the specific abnormality being treated, and can be determined by standard clinical techniques. In addition, in vitro assays can optionally be employed to help identify optimal dosage ranges. The precise dose of the active agent to be employed in the formulation will also depend on the route of administration, and the seriousness of the condition, and should be decided according to the judgment of the practitioner and each subject's circumstances. Suitable dosage ranges for administration are generally about 0.001 mg/kg to about 100 mg/kg of active agent per kilogram body weight. Effective doses can also be extrapolated from dose response curves derived from in vitro or animal model test systems. Suppositories generally contain active ingredient in the range of 0.5% to 10% by weight; oral formulations typically contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In yet another embodiment, the active agent can be delivered in a controlled release system. In one embodiment, a pump can be used (see, e.g. Langer, supra; Sefton, Crit. Ref. Biomed. Eng. 14:201-40 (1987); Buchwald et al., Surgery 88:507-16 (1980); Saudek et al., N. Engl. J. Med. 321:574-79 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al, Science 228:190-92 (1985); During et al., Ann. Neurol. 25:351-56 (1989); Howard et al., J. Neurosurg. 71:105-12 (1989)) (the disclosures of which are incorporated by reference herein).

In yet another embodiment, a controlled release system can be placed in proximity of the therapeutic target, thus requiring only a fraction of the systemic dose (see, e.g., Goodson, Medical Applications of Controlled Release, supra, Vol. 2, pp. 115-38 (1984)). Other controlled release systems are discussed in, for example, the review by Langer (Science 249:1527-33 (1990), which is incorporated by reference herein).

Following are examples that illustrate procedures for practicing the invention. These examples should not be construed as limiting. All percentages are by weight and all solvent mixture proportions are by volume unless otherwise noted.

Example 1

Materials and Methods

Reagents. All tissue culture reagents were obtained from Invitrogen Corporation (Carlsbad, Calif.) and MediaTech Inc (Herndon, Va.). SDF-1 was obtained from R&D Systems Inc (Minneapolis, Minn.) and Selleck Chemicals (Houston, Tex.), respectively. Recombinant human (rh)relaxin was a generous gift from Corthera Inc. (San Mateo, Calif.). The relaxin receptor antagonist B-R13/17K H2 was kindly provided by Dr. John D. Wade (Howard Florey Institute, Melbourne AU). All other reagents were obtained from Sigma-Aldrich (St. Louis, Mo.) unless otherwise indicated.

Isolation of CD34+ BMDEC. The study protocol was approved by the Institutional Review Board of the University of Florida, and written informed consent was obtained from each subject. Blood was collected from healthy controls by routine venipuncture into CPT™ Tubes with heparin (BD Biosciences, Franklin Lakes, N.J.), centrifuged at room temperature in a swinging bucket rotor for 20 minutes at 1800 RCF, the peripheral blood mononuclear cells (PBMCs) diluted with phosphate buffered saline supplemented with 2 mM EDTA (PBSE) and centrifuged for 10 minutes at 300 RCF. After washing the cell pellet, centrifugation was repeated. $3.3 \times 10^7$ PBMCs were resuspended in 100 µl of PBSE to which 33 µl of FcR blocking reagent (Miltenyi Biotec Inc., Auburn, Calif.) and 33 µl of magnetic microbeads conjugated with an anti-CD34 antibody was added. After incubation for 30 minutes at 4° C., the cells were diluted in 10× the volume of PBSE supplemented with 0.1% bovine serum albumin. The CD34+ BMDEC were positively selected using an automated magnetic selection autoMACS™ (Miltenyi Biotec Inc., Auburn, Calif.). The selected cells were confirmed to be CD34+ BMDEC by co-staining with PE conjugated anti-CD34 (Miltenyi Biotec Inc.) and FITC conjugated anti-CD45.

SDF-1/Relaxin Induced Chemotaxis. CD34+ BMDEC chemotaxis was carried out by staining the cells with Calcein-AM (Molecular Probes, Carlsbad, Calif.) prior to loading them into a Boyden Chamber. SDF-1 or rhRLX was loaded in the bottom chamber, which was overlaid with a polycarbonate membrane (8 µm pores) (Neuro Probe, Gaithersburg, Md.) coated with 10% bovine collagen and the cells were introduced into the top chamber. After 4.5 hours at 5% CO2 at 37° C., the percentage of cells that migrated was determined by collecting the media in the lower chamber and determining the relative fluorescence using a Synergy™ HT (Bio-Tek Instruments, Inc., Winooski, Vt.) with an excitation of 485±20 and an emission of 528±20 nm. For chemokinesis experiments rhRLX was also added to the top chamber with the cells. Migration was done in RPMI except in experiments with L-NAME when EGM-2™ (Lonza, Basel, Switzerland) media was utilized.

Detection of Nitric Oxide (NO) produced by cells. CD34+ BMDEC or mouse BMDEC colonies were cultured on a 35 mm dish with a glass bottom insert (MatTek Corp., Ashland, Mass.). Bioavailable NO was determined as previously described (Shah, R., Beem, E., Sautina, L., Zharikov, S. I., and Segal, M. S. 2007. Mitomycin- and calcineurin-associated HUS, endothelial dysfunction and endothelial repair: a new paradigm for the puzzle? *Nephrol Dial Transplant* 22:617-620). Briefly, BMDEC were incubated with 5 µM 4-amino-5-methylamino-2',7'-difluzorofluorescein (DAF-FM) diacetate (Molecular Probes™, Invitrogen detection technologies, Carlsbad, Calif.) for 30 minutes at 37° C. in the dark. Excess extracellular probe was removed by washing in HBSS followed by incubation for 10 minutes at room temperature to allow for probe de-esterification. DAF-FM fluorescence increases by about 160-fold when it reacts with NO. Green fluorescence was measured using the inverted fluorescent Carl Zeiss Axiovert 200M microscope equipped with a CCD camera and Slidebook software (v.4.1; Intelligent Imaging Innovations, Inc. Denver, Colo.). Fluorescence intensity was measured in 20-30 cells per field in at least 6 fields per well. Alternatively, imaging was performed using a confocal microscope at excitation and emission maxima of 495 and 515 nm, respectively. Intensity of fluorescence was quantified using LSM 510 (version 3.0 SP3) software for the Carl Zeiss Laser Scanning Microscope.

Mouse Protocols. All animal procedures were performed according to protocols approved from the Institutional Animal Care and Use Committee and complied with the Guide for the Care and Use of Laboratory Animals. Male Rxfp1−/− mice aged ~15 months (Kamat, A. A., Feng, S., Bogatcheva, N. V., Truong, A., Bishop, C. E., and Agoulnik, A. I. 2004. Genetic Targeting of Relaxin and Insulin-Like Factor 3 Receptors in Mice. *Endocrinology* 145:4712-4720) and Rxfp2−/− mice aged 4-8 months (Gorlov, I. P., Kamat, A., Bogatcheva, N. V., Jones, E., Lamb, D. J., Truong, A., Bishop, C. E., McElreavey, K., and Agoulnik, A. I. 2002. Mutations of the GREAT gene cause cryptorchidism. *Hum Mol Genet* 11:2309-2318), and their respective C57BL/6J and FVB wild-type littermates, as well as female C57BL/6J mice (the majority of which were aged between 2-4 months) from Harlan (Indianapolis, Ind.) were utilized.

Chimeric GFP mice were generated as previously described (Asahara, T., Murohara, T., Sullivan, A., Silver, M., van der Zee, R., Li, T., Witzenbichler, B., Schatteman, G., and Isner, J. M., 1997, "Isolation of Putative Progenitor Endothelial Cells for Angiogenesis" *Science* 275:964-966). Briefly, GFP transgenic mice (C57BL/6J background) obtained from Jackson Laboratory (Bar Harbor, Me.), express GFP in every cell driven by chicken β-actin promoter and cytomegalovirus intermediate early enhancer. Wild-type C57BL/6J mice were irradiated with 950 rads and injected with bone marrow cells (1×106) from GFP mice into the retro orbital sinus. Chimeric mice were allowed to stably engraft for 6-10 months prior to subcutaneous injection of the Matrigel pellets. The mice were housed under standard conditions (12:12 light/dark cycle) with access to PROLAB RMH 2000 feed containing 0.32% sodium (PME Feeds Inc., St. Louis, Mo.) and water ad libitum.

Osmotic pump Implantation. Briefly, mice were anesthetized with isoflurane using a portable anesthesia machine (Summit Medical, Bend, Oreg.). Alzet osmotic pumps (Model 1007D 7 day infusion, or 1002 14 day infusion, Durect Co.) containing rhRLX or vehicle (20 mM sodium carbonate, pH 5.2) was then implanted subcutaneously on the back. The rate of infusion of rhRLX was 1 μg/hour. This yielded an average circulating concentration of 39.6±4.1 ng/ml.

Mouse BMDEC Enumeration. After 5 days of rhRLX or vehicle administration, the mice were anesthetized with pentobarbital and the whole peripheral blood were collected via cardiac perfusion with 2-3 ml heparin solution in saline (100 IU/ml) (Diao, Y., Xue, J., and Segal, M. S. 2005. A novel mouse model of autologous venous graft intimal hyperplasia. *J Surg Res* 126:106-113). Blood collected from the mouse was layered onto Ficoll® 400 and centrifuged at 400×g for 30 minutes at 10° C. The buffy coat was collected, washed twice in PBS/2% fetal bovine serum, resuspended in 3 ml Endocult Media (Stem Cell Technologies, Vancouver, BC, Canada), and plated onto a 60 mm tissue culture plates coated with fibronectin and containing 3 ml of EGM-2™. After 5-7 days the number of colony forming units (CFU) were counted. They were identified to be BMDEC based on their ability to stain with 1,1'-dioetadeeyl-3,3,3',3'-tetramethylindocarboeyanine perchlorate acetylated low density lipoprotein (DiI-AcLDL) (Invitrogen) and *Ulex europaeus* 1 (Sigma).

Flow cytometry. Three mL of RBC lysis buffer (BD Biopharmacies) was added to 20 μL of heparinized peripheral blood and after 15 minutes in the dark, was centrifuged at 300 g ×10 minutes, the supernate decanted, and cells resuspended in 100 μL of PBS. The antibodies PerCP anti-mouse Ly-6A/E (Sca-1) (Clone: D7 BioLegend), PE anti-mouse CD117 (c-Kit) (Clone: 2B8 BioLegend) and APC Mouse Lineage Antibody Cocktail (BD Biosciences) were added to the cells and incubated for 15 minutes at room temperature. The cells were washed with 2-3 mL of PBS, centrifuge at 300 g×10 minutes and supernatant decanted. After resuspending in 300 μL of PBS/1% BSA/0.01% NaN3 and fixed in 2% paraformaldehyde the cells were analyzed by FACScaliber (BD). Control staining with isotype-matched antibodies was carried out in parallel. Data analysis was performed using FCS Express 3.0 (De Novo Software, Ontario, Canada).

Isolation of Bone Marrow Cells from Mice. Mice were euthanized with pentobarbital, the femurs and tibias removed and placed in a 35 mm dish (on ice), and the bones sterilized with 70% ethanol for 20 seconds. After cutting the ends of both bones off with micro-surgical scissors, the medullary cavities were flushed with phosphate buffered saline (PBS) with a syringe with a 25 G ⅝" needle. To remove bits of bone and tissue chimps, the PBS containing the marrow was filtered through a sterile 40-μm nylon mesh (BD Biosciences), collected into a 15-ml of medium, and the cells centrifuged at 300 g for 15 minutes at room temperature. The cells were washed twice with PBS/2% fetal bovine serum, resuspended in EGM-2™ medium (Lonza) and plated onto 60 mm tissue culture plates coated with fibronectin.

Plasma Relaxin Concentration. Plasma rhRLX concentrations were measured in duplicate using a commercially available ELISA that has been validated for mouse plasma (R&D Systems, Minneapolis, Minn.). The assay typically yielded a standard curve with $R2=0.998$ with a minimum detectable dose (MDD) of <10 pg/ml. The intra-assay precision (average CV of the unknowns) was <6.7±1.3% and the inter-assay precision (average of CV of the standards was 6.5±2.1%. Plasma H2 relaxin was below the MDD in vehicle-treated mice.

In vivo neoangiogenesis assay. Two 250 μl Matrigel implants were injected into each mouse, one injection containing 100 ng/ml relaxin and the other containing vehicle. Subcutaneous injections were made on the right (relaxin pellet) and left (vehicle pellet) sides of the midventral abdominal region. Seven days after injections mice were anesthetized, perfused with saline and heparin, and blood was collected from the heart. After the blood was collected, the mice were perfused with 4% paraformaldehyde and the Matrigel pellets were removed from the abdomen, placed in 4% paraformaldehyde, and stored at 4° C. for 12-24 hours. The pellets were then washed 3 times with 1×PBS, paraffin embedded, sectioned, and stained with anti-GFP and anti-MECA-32 antibodies. Image analysis of the staining was performed using the AutoMeasure Plus module of the image acquisition and analysis software AxioVision v.4.5. (Carl Zeiss). Average area of fluorescent cells was calculated from three fields per slide and 3 slides per pellet by summing all areas of fluorescence divided by total area analyzed.

Statistical analysis: Data are expressed as mean±standard deviation. Statistical analysis was carried out using Student's t Test, Mann-Whitney Rank Sum Test, or One Way Analysis of Variance with Multiple Comparisons performed by the Holm-Sidak or Dunn's Method.

Results

Relaxin is a chemoattractant for human CD34+ BMDEC. To establish whether relaxin could increase BMDEC number and function, e.g., migration and NO production, the experiments described herein were conducted. CD34 was used as a marker of progenitor populations, including BMDEC, that promote vasculogenesis and neovascularization, since functional studies performed on only true BMDEC (the very rare CD34+/CD45−/VEGFR2+ or CD133+/CD45−/VEGFR2+ cells) would require a prohibitively large amount of blood.

Figure 1B:
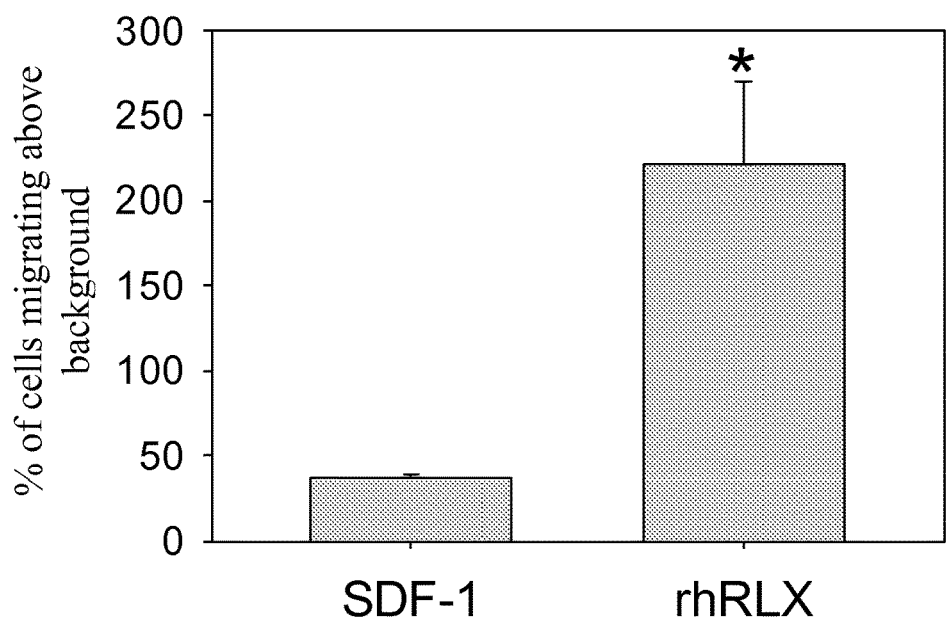
Figure 1C:
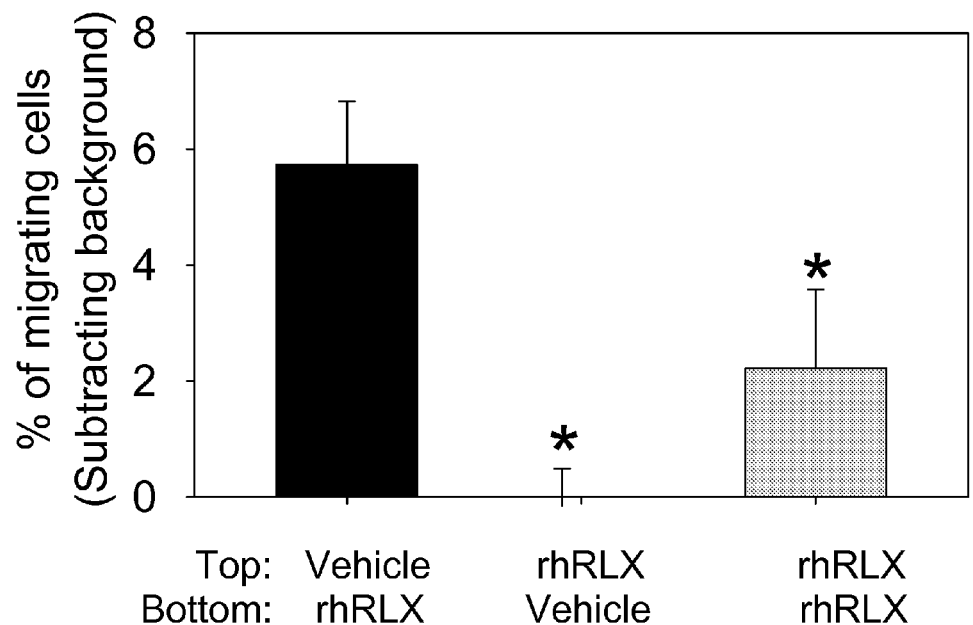

The experiments described herein demonstrated that CD34+ BMDEC isolated from the peripheral blood of healthy volunteers migrated in response to increasing concentrations of rhRLX with a threshold dose of 10 ng/ml ($p<0.001$ versus 0 ng/ml, FIG. 1a). CD34+ BMDEC isolated from the peripheral blood of healthy volunteers migrated in response to rhRLX to a greater extent than to stromal derived factor-1, SDF-1, a major chemokine for CD34+ cells (FIG. 1b). This stimulation of migration was not a chemokinetic effect, since rhRLX added to the top well or both wells of the Boyden chamber did not result in an increase in migration (FIG. 1c).

Figures 2A, 2B:
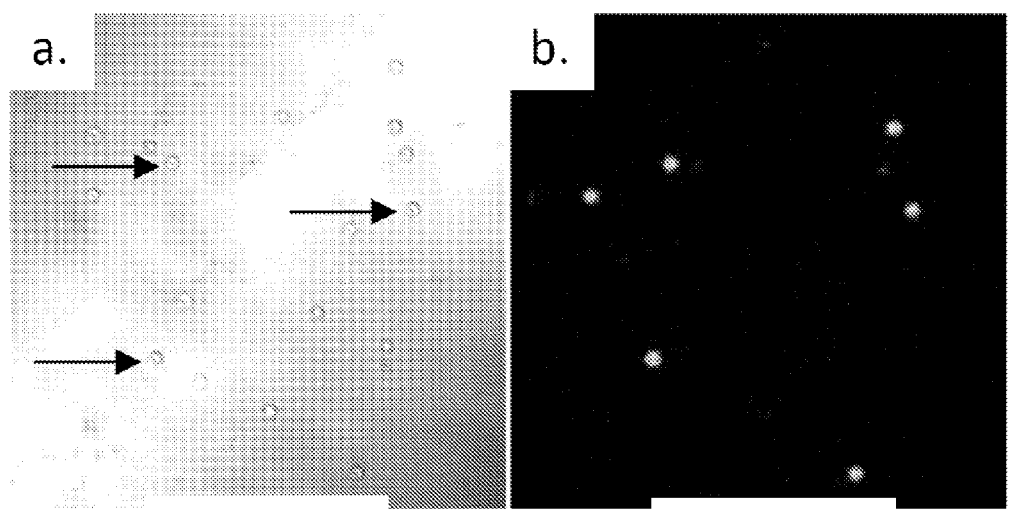
FIG. 2. CD34+ BMDEC produce NO in response to rhRLX. Human CD34+ BMDEC were isolated in the absence (A & B) and presence (C & D) of 100 µM L-NAME and then incubated with DAF-FM prior to imaging with a confocal microscope. A & C are brightfield images of (B & D), respectively, the same fields imaged with 495 nm excitation and 515 nm emission. Arrows indicate some of the CD34+ BMDEC. 200×. E. CD34+BMDEC were isolated from a healthy volunteer and labeled with DAF-FM for 30 minutes before removing probe and waiting 10 minutes for deesterification. The cells were monitored for 30 minutes, to confirm a stable baseline of bioavailable NO, before vehicle (o; arrow) or 50 ng/ml of rhRLX (•; arrow) was added to the CD34+ cells. Shown is the mean fluorescence (±SD) of at least 8 cells in which fluorescence was continuously monitored. *$p<0.01$ versus last baseline value. (F). BMDEC-CFU were isolated from a healthy volunteer and labeled with DAF-FM. After 30 minutes to stabilize NO baseline, the indicated concentration of rhRLX was added and after 30 minutes fluorescence was determined. Shown is mean (±SD). *$p<0.001$ versus 0 ng/ml of rhRLX. (G) Cells were incubated with 10 µM L-Name prior to being placed in the Boyden chamber with 50 ng/ml of rhRLX. The mean percentage (±SD) of fluorescence of cells migrating relative to control is shown. *$p<0.001$ versus all other treatments.
Figures 2C, 2D:
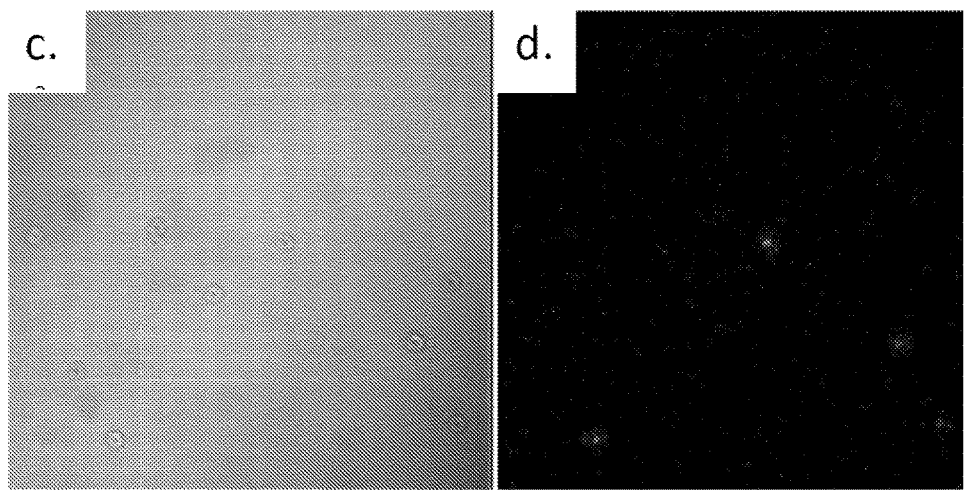
Figure 2E:
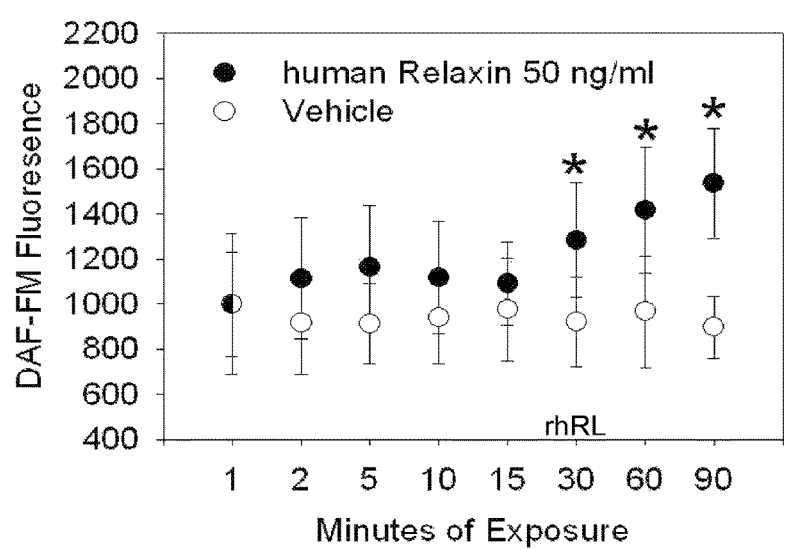
Figure 2F:
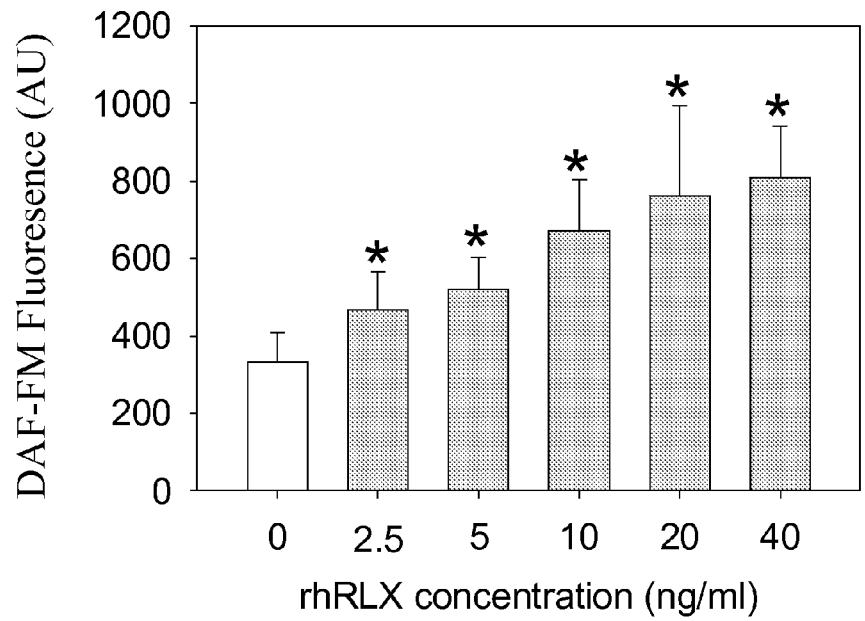
Figure 2G:
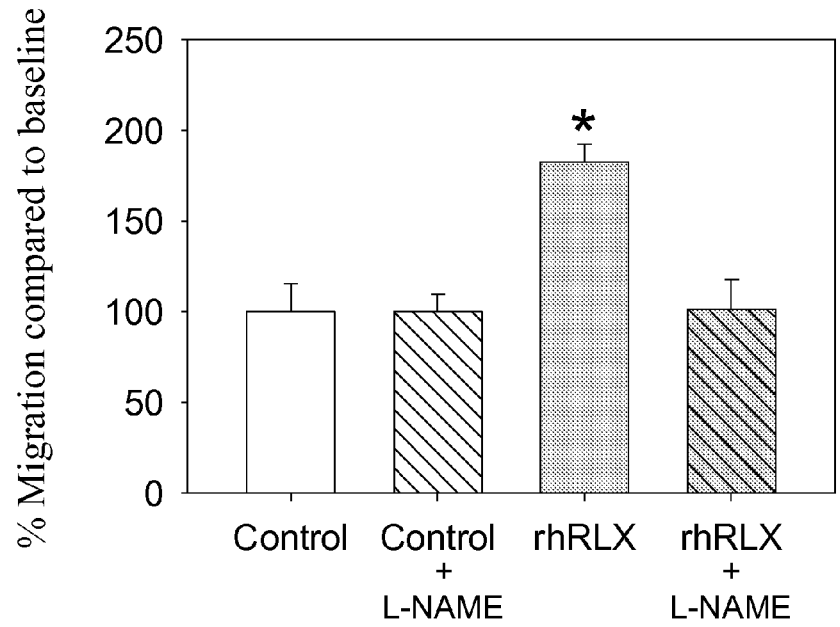

Relaxin stimulates NO in human CD34+ BMDEC via PI3K/Akt. Previously NO has shown to be critical to BMDEC function (Asahara, T., Murohara, T., Sullivan, A., Silver, M., van der Zee, R., Li, T., Witzenbichler, B., Schatteman, G., and Isner, J. M., 1997, "Isolation of putative progenitor endothelial cells for angiogenesis" *Science* 275: 964-967; Dimmeler, S., Dernbach, E., and Zeiher, A. M., 2000, "Phosphorylation of the endothelial nitric oxide synthase at Ser-1177 is required for VEGF-induced endothelial cell migration" *FEBS Letters* 477:258-262; Dimmeler, S., Aicher, A., Vasa, M., Mildner-Rihm, C., Adler, K., Tiemann, M., Rutten, H., Fichtlscherer, S., Martin, H., and Zeiher, A. M., 2001, "HMG-CoA reductase inhibitors (statins) increase endothelial progenitor cells via the PI 3=kinase/Akt pathway" *J Clin Invest* 108:391-397; Aicher, A., Heeschen, C., Mildner-Rihm, C., Urbich, C., Ihling, C., Technau-Ihling, K., Zeiher, A. M., and Dimmeler, S., 2003, "Essential role of endothelial nitric oxide synthase for mobilization of stem and progenitor cells" *Nat Med* 9:1370-1376; and Llevadot, J., Murasawa, S., Kureishi, Y., Uchida, S., Masuda, H., Kawamoto, A., Walsh, K., Isner, J. M., and Asahara, T., 2001, "HMG-CoA reductase inhibitor mobilizes bone marrow-derived endothelial progenitor cells" *J Clin Invest* 108: 399-405), thus experiments described herein were conducted to establish whether relaxin increased BMDEC NO levels using the method of single cell determination (Sautina, L., Sautin, Y., Beem, E., Zhou, Z., Schuler, A., Brennan, J., Zharikov, S. I., Diao, Y., Bungert, J., and Segal, M. S. "Induction of nitric oxide by erythropoietin is mediated by the {beta} common receptor and requires interaction with VEGF receptor 2" *Blood* 115:896-905) (FIG. 2a-d). The results from the experiments indicate incubation with rhRLX leads to a rapid increase in intracellular NO concentrations (FIG. 2e) with a threshold as low as 2.5 ng/ml rhRLX (FIG. 2f). To determine whether stimulation of NO underlies relaxin's chemotactic effect on BMDEC, NOS was inhibited with 10 μM of the arginine analog L-NAME, a low concentration that does not lower basal levels of NO, but effectively blocks agonist-induced increases in NO (Schuler, A., Sautina, L., Zharikov, S., Perrault, C., Tran-Son-Tay, R., Beem, E., and Segal, M. S., 2005, "Epoetin alfa Enhances Chemotaxis of Circulating Endothelial Progenitor Cells to SDF-1 and Stimulates Intracellular Nitric Oxide Production" *In American Society of Nephrology*. Philadelphia, Pa.). The ability of relaxin to stimulate chemotaxis was blocked by low level L-NAME, but importantly the basal level of migration was unaffected by these low levels of L-NAME (FIG. 2g).

Figure 3A:
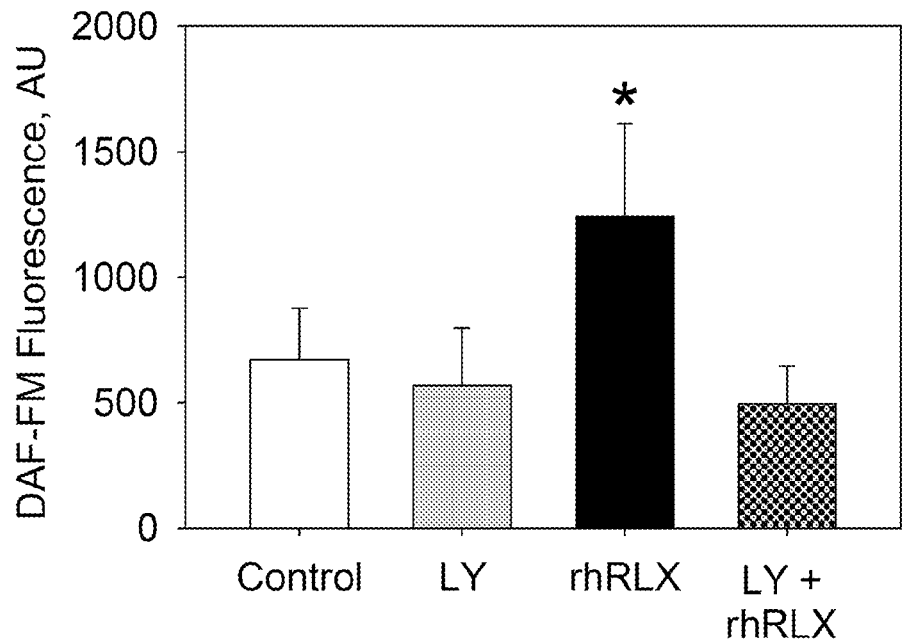
FIG. 3. Relaxin stimulates NO production via PI3K/Akt. (A) Human CD34+ BMDEC were isolated from a healthy volunteer and pretreated with the PI3K inhibitor LY294002 (10 µM) for 30 minutes as indicated prior to the addition of DAF-FM and continued incubation with LY294002 (LY). After 30 minutes of monitoring, to confirm that bioavailable NO was stable, either vehicle (Control) or 100 ng/ml of rhRLX was added to the CD34+ BMDEC and NO was measured again after 30 minutes. Fluorescence was determined for each condition in at least 30 cells within two separate wells. Shown is mean (±SD). * p<0.001 versus all other conditions. (B) CD34+ BMDEC were isolated from a healthy volunteer and pretreated with the Akt inhibitor MK2206 (20 nM) for 30 minutes as indicated prior to the addition of DAF-FM and continued incubation with MK2206. After 30 minutes of monitoring, to confirm that bioavailable NO was stable, either vehicle (Control) or 50 ng/ml of rhRLX was added to the CD34+ BMDEC and NO was measured again after 30 minutes. Fluorescence was determined for each condition in two wells for at least 30 cells per well. Shown is mean (±SD). *p<0.001 versus control. There is a significant difference between control and MK2206, p=0.025, but no difference between MK2206 and MK2206+rhRLX treated cells.
Figure 3B:
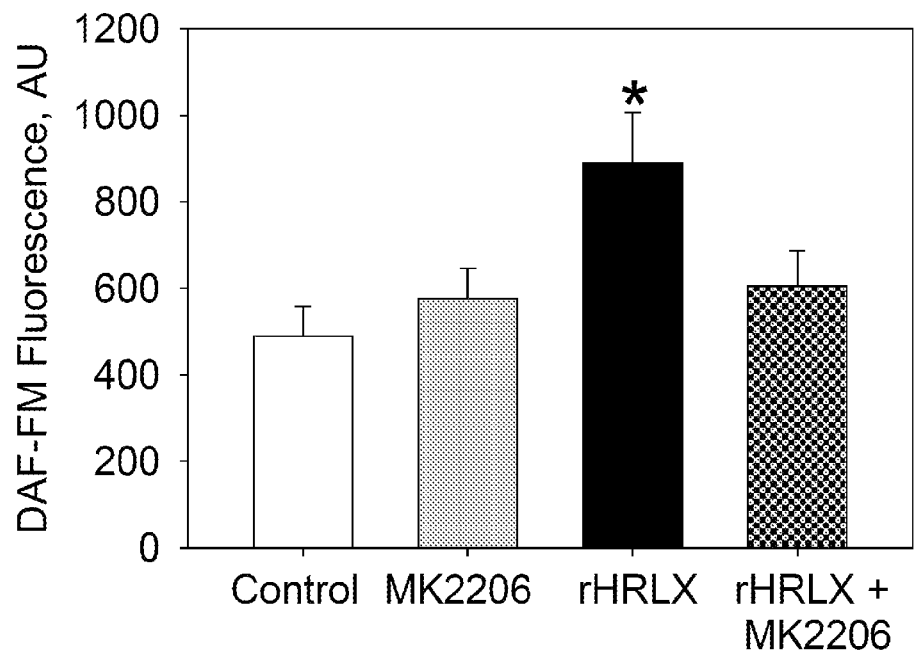

The PI3K/Akt pathway was previously identified as being crucial to the rapid production of NO by endothelial cells and consequently rapid relaxation of small arteries (McGuane, J., Debrah, J., Sautina, L., Rubin, J., Novak, J., Segal, M., and Conrad, K. Submitted. Relaxin induces rapid dilation of rodent small renal and human subcutaneous arteries via PI3 kinase and nitric oxide. *Endocrinology*, 2011 July; 152(7):2786-96. Epub 2011 May 10). Thus, the PI3K inhibitor LY294002 was utilized in the experiments described herein to interrogate the role of PI3K in rhRLX-stimulated NO production in BMDEC. Pretreatment with LY294002 blocked rhRLX-stimulated increase in NO by CD34+(FIG. 3a). In addition pretreatment with the Akt inhibitor MK2206 (Hirai, H., Sootome, H., Nakatsuru, Y., Miyama, K., Taguchi, S., Tsujioka, K., Ueno, Y, Hatch, H., Majumder, Pan, B.-S., et al. "MK-2206, an Allosteric Akt Inhibitor, Enhances Antitumor Efficacy by Standard Chemotherapeutic Agents or Molecular Targeted Drugs In vitro and In vivo" *Molecular Cancer Therapeutics* 9:1956-1967) also prevented rhRLX stimulation of NO in BMDEC (FIG. 3b). Taken together, these results suggest that the PI3K/Akt pathway is integral to relaxin's ability to stimulate NO in CD34+ BMDEC.

Figure 4H:
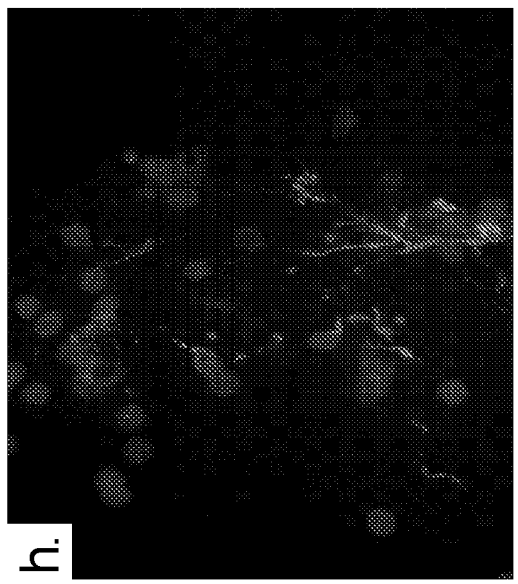
FIG. 4. Relaxin increases circulating BMDEC in mice by colony assay and flow cytometry. A. BMDEC-CFU are counted after 5 days of culture and a brightfield view of colonies is shown at 100× (B) True BMDEC-CFUs demonstrate *Ulex europaeus* 1 staining 200× (C), DiI-AcLDL uptake 200×, D. dual staining in a merged image of Ulec and DiI-AcLDL staining, 200×. Instead of staining the BMDEC-CFU cells can be propagated for months. (E) Brightfield view of cells after 3 months of propagation taking on a cobblestone, endothelial, monolayer appearance. (F) Brightfield view of propagated cells that were trypsinized and plated onto a coverslip for immunostaining with anti-von-Willebrand Factor and/or anti-MECA 32. (G) Merged image of cells in (F) stained with anti-von-Willebrand Factor (red) and the nuclear stain DAPI (blue). 400×. (H) Merged image of another coverslip stained with anti-von-Willebrand Factor (red), anti-MECA 32 (green) and the nuclear stain DAPI (blue). 630× (H). (H-K) Mice were implanted with osmotic pumps containing vehicle (I and J) or rhRLX (K and L) and after 5 days the peripheral blood was collected and stained with fluorochrome-conjugated monoclonal antibody to mouse endothelial cell markers Lin, Sca-1, cKit, Flk1. The gated cells were analyzed for Sca-1 and Lin characteristics (I and K) and the subpopulation of Sca1+ cells were analyzed for Flk1 and cKit expression (J and L). Background staining was corrected by use of isotype controls for all markers. Percentages shown are percent of gated cells, not total lymphocytes.
Figures 4F, 4G:
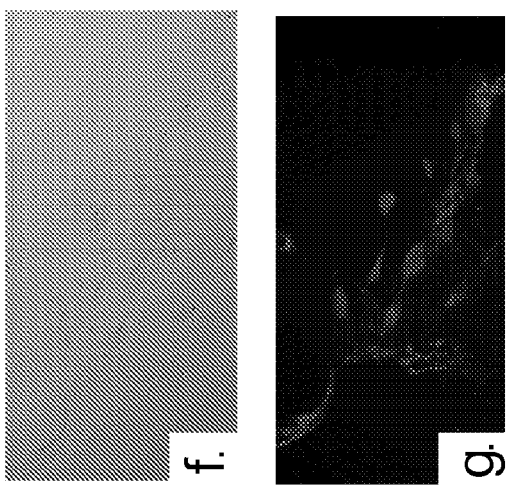
Figure 4E:
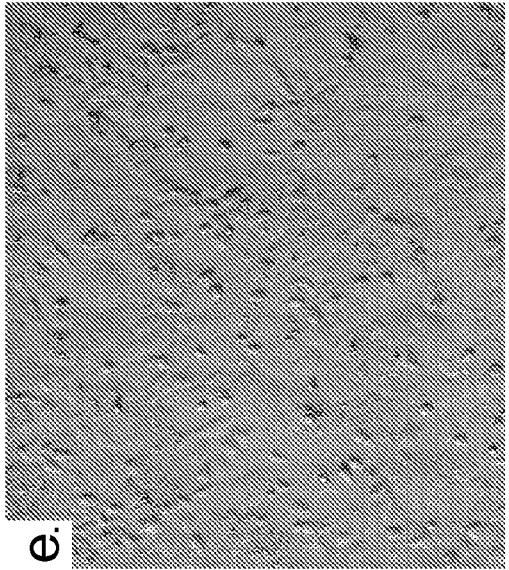
Figure 4I:
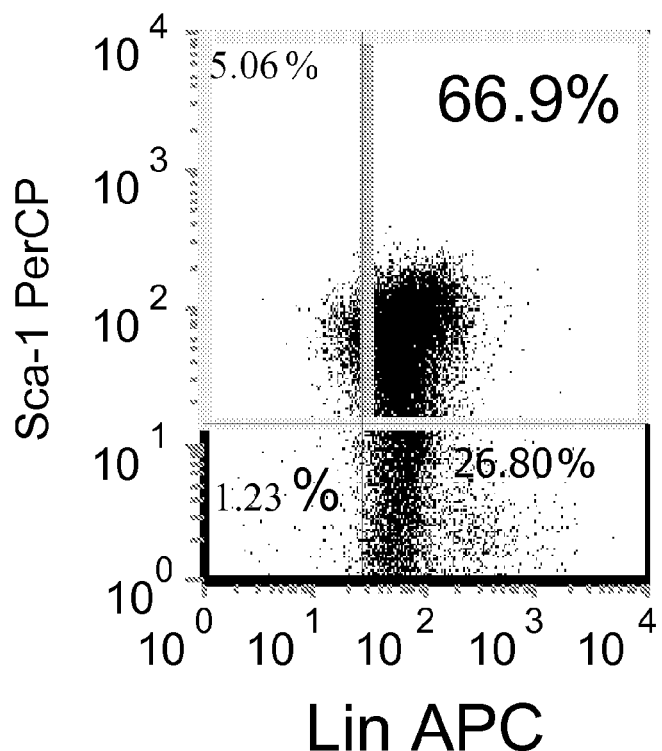
Figure 4J:
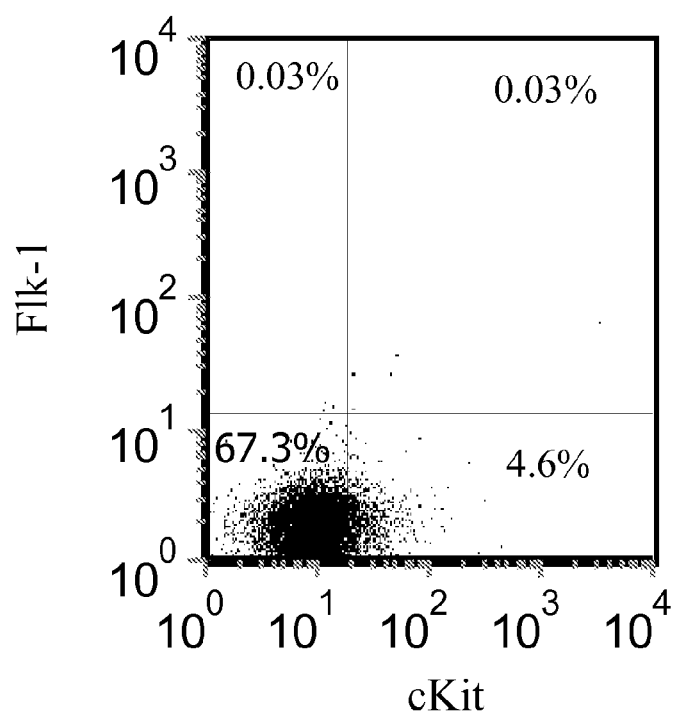
Figure 4K:
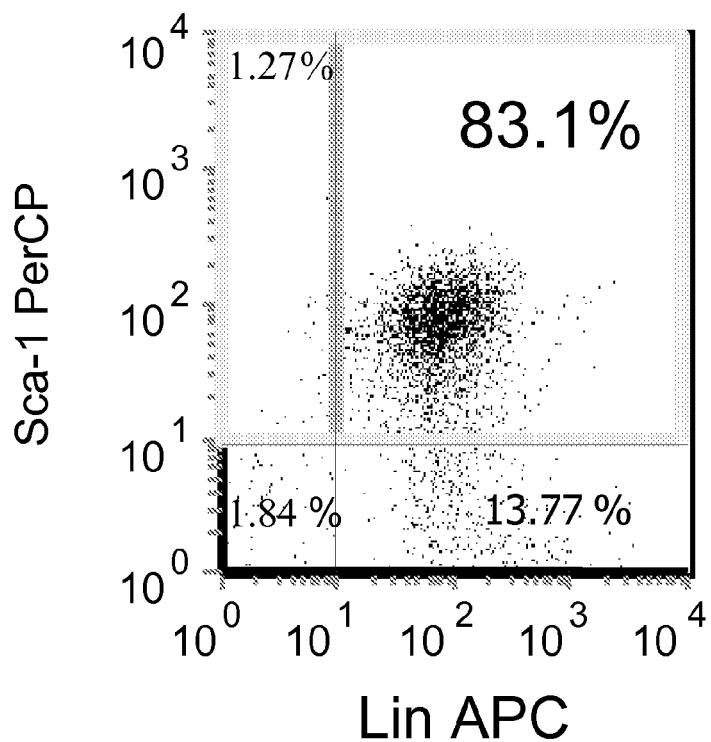
Figure 4L:
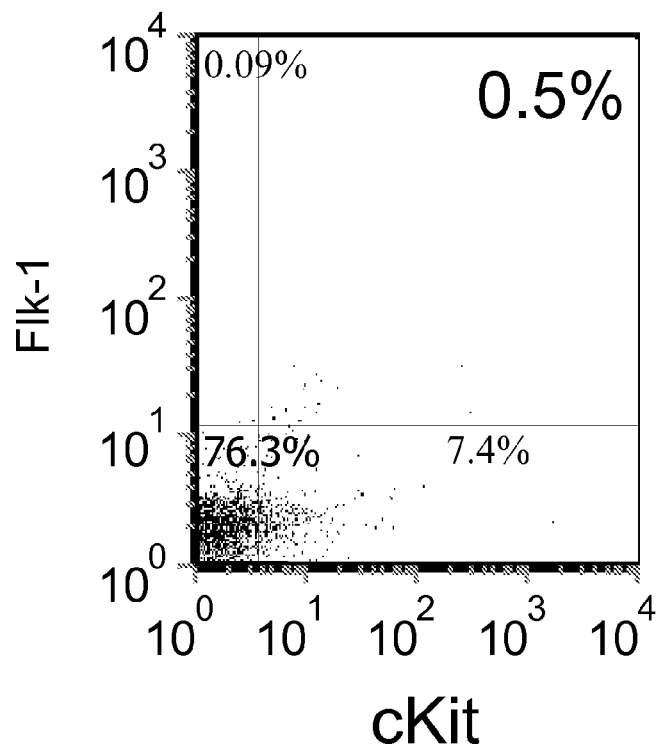

Relaxin increases circulating BMDEC in vivo. The effect of relaxin on circulating BMDEC in vivo was assessed using two different methods: 1) BMDEC colony assay, and 2) FACS analysis by determining the percentage of Sca+, Flk+, cKit+ cells in the peripheral blood (Lemarie, C. A., Shbat, L., Marchesi, C., Angulo, O. J., Deschenes, M.-E., Blostein, M. D., Paradis, P., and Schiffrin, E. L., "Mthfr deficiency induces endothelial progenitor cell senescence via uncoupling of eNOS and downregulation of SIRT1" *American Journal of Physiology—Heart and Circulatory Physiology*). In the BMDEC colony assay, endothelial colonies from the peripheral blood that stain with *Ulex europaeus* 1 and DiI-AcLDL can be seen after 1 week in culture (FIG. 4a-d). These colonies can be continuously cultured for over 3 months when they take on a more endothelial appearance (FIG. 4e) and express von Willebrand Factor and MECA-32 (FIG. 4f-g), thus confirming their endothelial progenitor phenotype. Using the BMDEC colony assay, mice implanted with osmotic pumps containing rhRLX (n=9 mice) had almost 2-fold more colonies forming units (CFU) versus to the vehicle-infused group (7.3±4.0 versus 3.9±1.4 CFU/mice, respectively; p=0.022).

Flow cytometry was used as described herein to confirm the effect of relaxin on BMDEC number. Using the same rhRLX and vehicle treatment regimens, the number of Sca+, Flk+, cKit+ cells was determined. In mice treated with vehicle and rhRLX (n=15 each) 0.002±0.0001% and 0.032±0.0005% of total lymphocytes were Sca+, Flk+, cKit+, respectively (p=0.013). Representative FACS analyses are shown in FIGS. 4a-d.

Figure 5A:
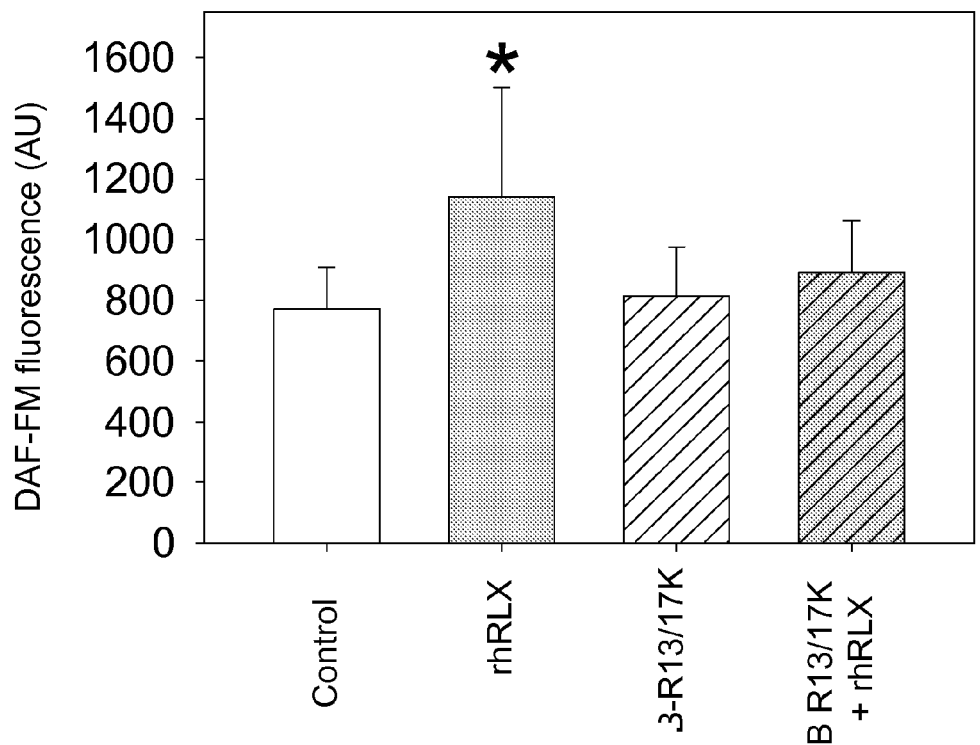
FIG. 5. Relaxin activates BMDEC through the RXFP1 relaxin receptor. (A) The peptide B-R13/17K H2 (H2), a relaxin antagonist, was added as indicated to CD34+ BMDEC at a concentration of 1 μM in the presence or absence of rhRLX (50 ng/ml). Shown is the DAF-FM fluorescence in AU (±S.D) of 2 wells, 20 cells per well. *p<0.002 versus all other treatments. Shown is a representative of 3 experiments. (B) BMDEC were isolated from the bone marrow of wild-type litter-mates and Rxfp1 or Rxfp2 knock-out mice and treated with vehicle (black bars) or rhRLX 50 ng/ml (white bars) for 10 minutes prior to the determining intracellular bioavailable NO by DAF-FM. The NO fluorescence from at least 20 cells was analyzed for each mouse. Shown is the mean DAF-FM fluorescence in AU (±SD). *p<0.009 versus vehicle treated cells; \p<0.05 versus untreated cells. n indicates the number of mice studied. (C) Wild-type (+/+) litter-mates and Rxfp1 and Rxfp2 knock-out (−/−) mice were implanted with osmotic pumps containing rhRLX and after 5 days their blood was collected and BMDEC-CFU were determined. Shown is the number of BMDEC (±SD). *p<0.01 versus Rxfp1+/+. n indicates the number of mice studied.
Figure 5B:
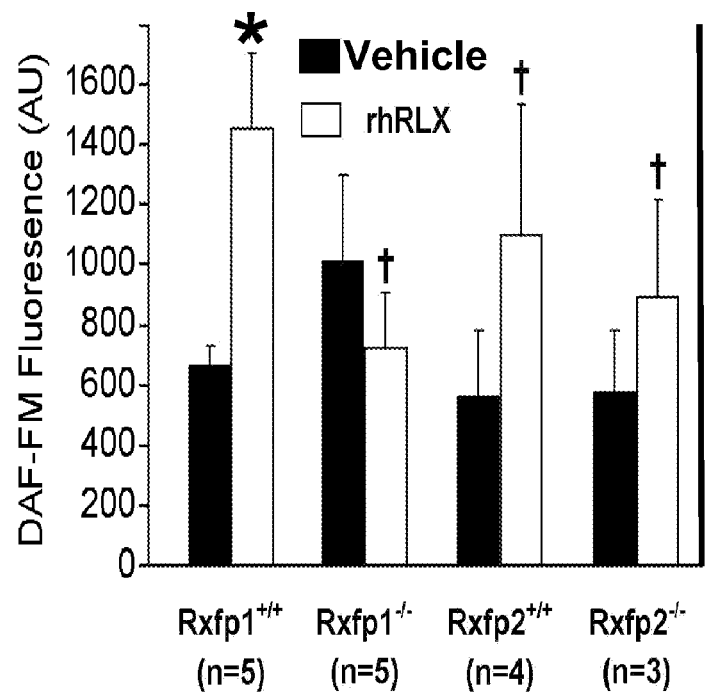

Relaxin-induced BMDEC mobilization and NO stimulation is mediated by the RXFP1 relaxin receptor. Relaxin increases CD34+ BMDEC NO production and migration in vitro and mobilizes BMDEC in vivo. To determine which of the relaxin receptors may mediate its effects on BMDEC, the newly developed human relaxin-2 antagonist, B-R13/17K H2 (27, 28) was tested as described herein. This antagonist inhibited the increase in NO in response to rhRLX treatment (FIG. 5a) consistent with a role for the RXFP1 receptor in mediating NO production by rhRLX. To more definitively demonstrate that the RXFP1 receptor is responsible for mediating the effect of relaxin on BMDEC mobilization, Rxfp1 and Rxfp2 knock-out mice were employed. Bone marrow cells isolated from the Rxfp2 knock-out and FVB wild-type littermates both showed a significant increase in NO in response to rhRLX (FIG. 5b). However, bone marrow cells from Rxfp1 knock-out mice failed to demonstrate an increase in NO when treated with rhRLX in contrast to the C57BL/6J wild-type littermates (FIG. 5b).

Figure 5C:
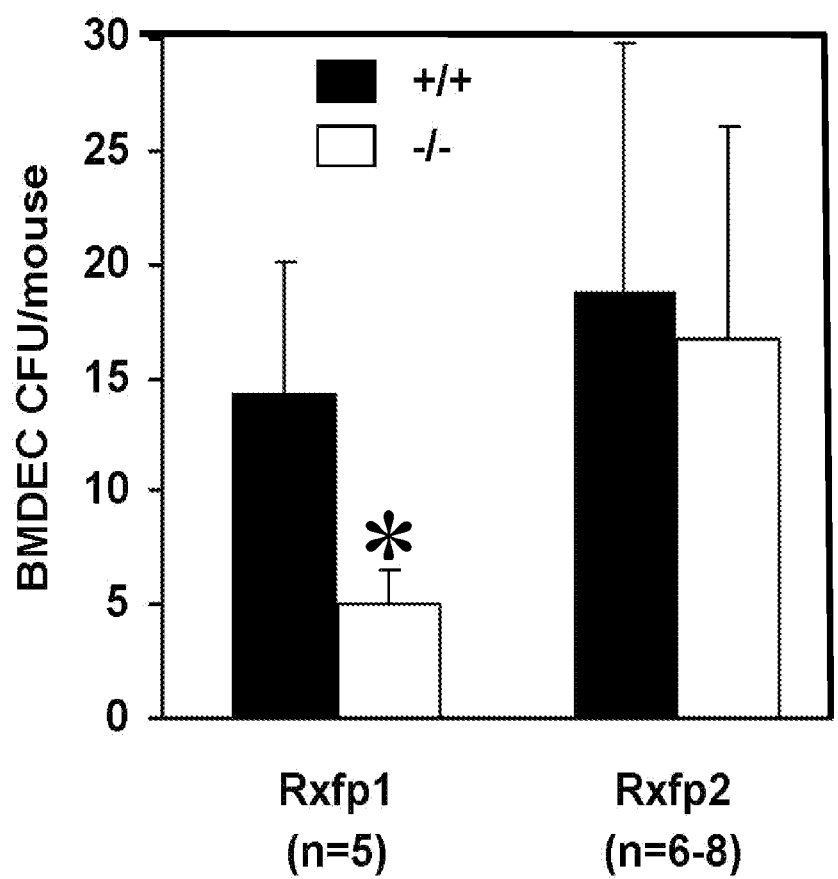

Consistent with these findings, infusion of rhRLX via osmotic pump led to an increase in circulating BMDEC-CFU in both Rxfp2 knock-out and wild-type littermates (FIG. 5c), whereas there were significantly less circulating BMDEC-CFU in rhRLX-infused Rxfp1 knock-out mice versus their wild-type counterparts (FIG. 5c). All wild-type and knock-out mice treated with vehicle had comparable number of BMDEC-CFU (data not shown).

Figure 6A:
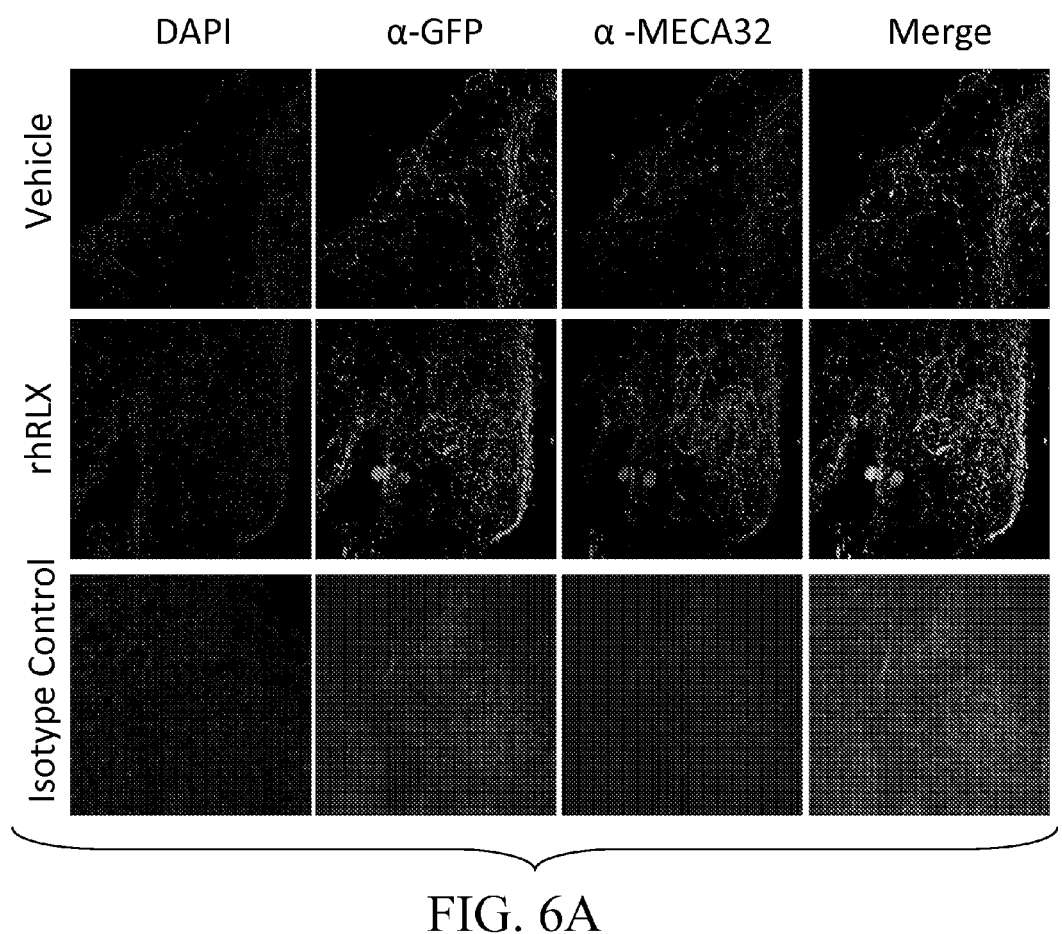
FIG. 6. Relaxin recruits BMDEC into areas of neovascularization. (A) Chimeric mice (wild-type mice with GFP bone marrow) were implanted with Matrigel pellets impregnated with vehicle or rhRLX, as indicated, and after 7 days the pellets were isolated, embedded in paraffin, sectioned, and stained with DAPI, a pan-endothelial cell antigen monoclonal antibody MECA-32, anti-GFP, or isotype control antibodies as indicated and imaged using conventional fluorescent microscopy. (B) Same as in (A) except slides imaged using confocal microscopy. (C) Percentage of area that fluoresces red (by epifluorescence) indicating MECA-32 staining. Shown is average area of 3 fields from 6 different sections from 9 pellets for each treatment. *p<0.001 by paired t-test. (D) Percentage of area that expresses dual fluorescence (by epifluorescence) indicating dual MECA-32 and GFP staining. Shown is average area of 3 fields from 6 different sections from 9 pellets. *p<0.001 by paired t-test.
Figure 6B:
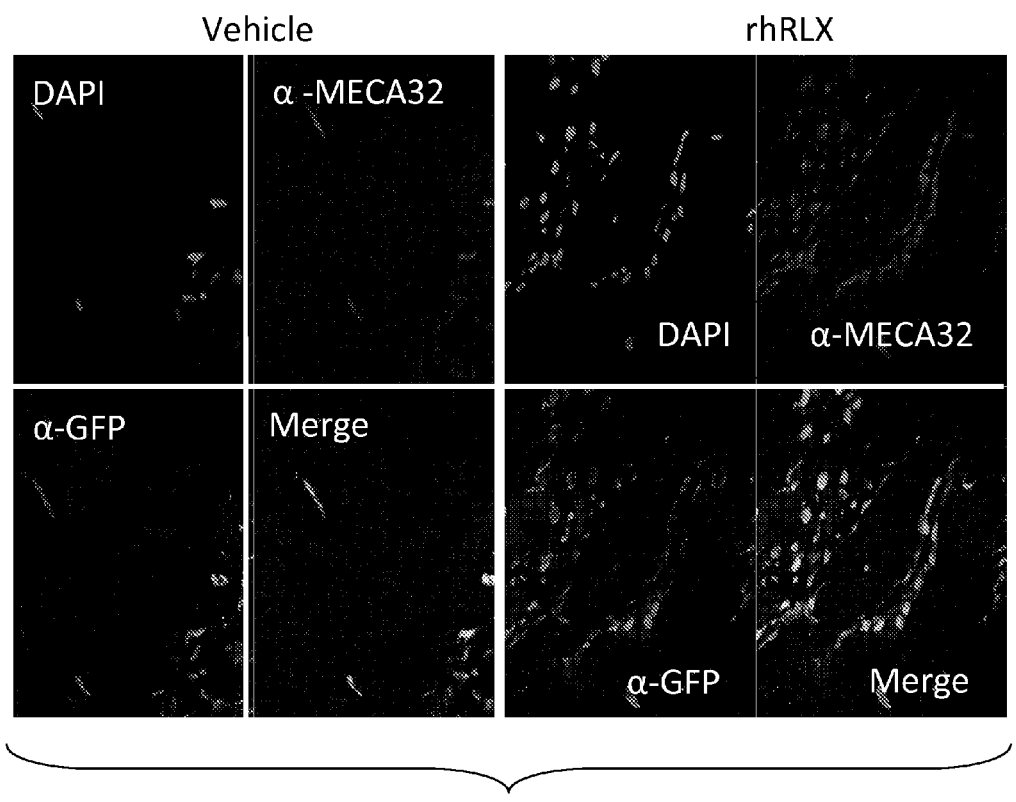
Figure 6C:
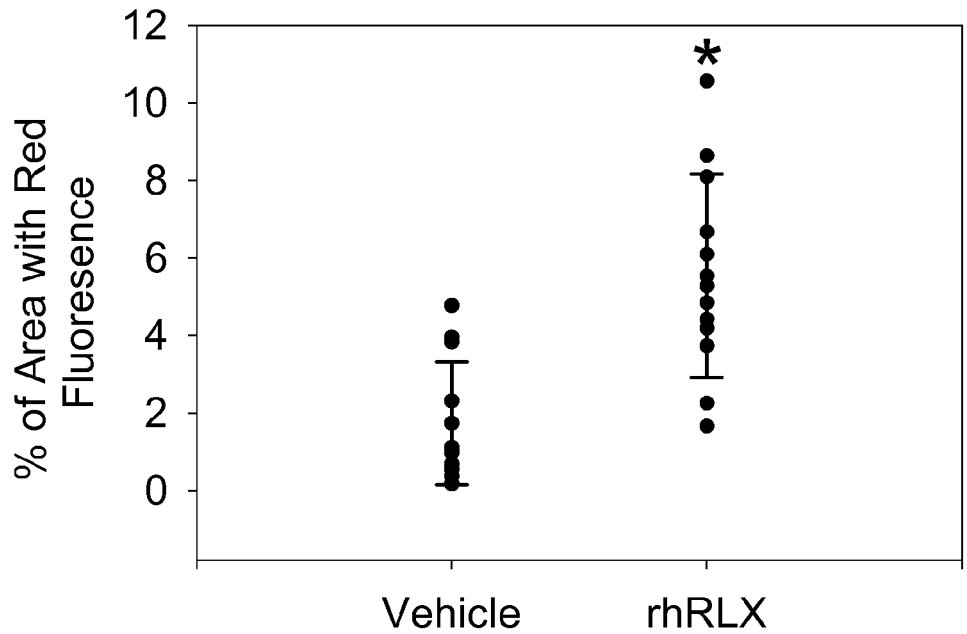
Figure 6D:
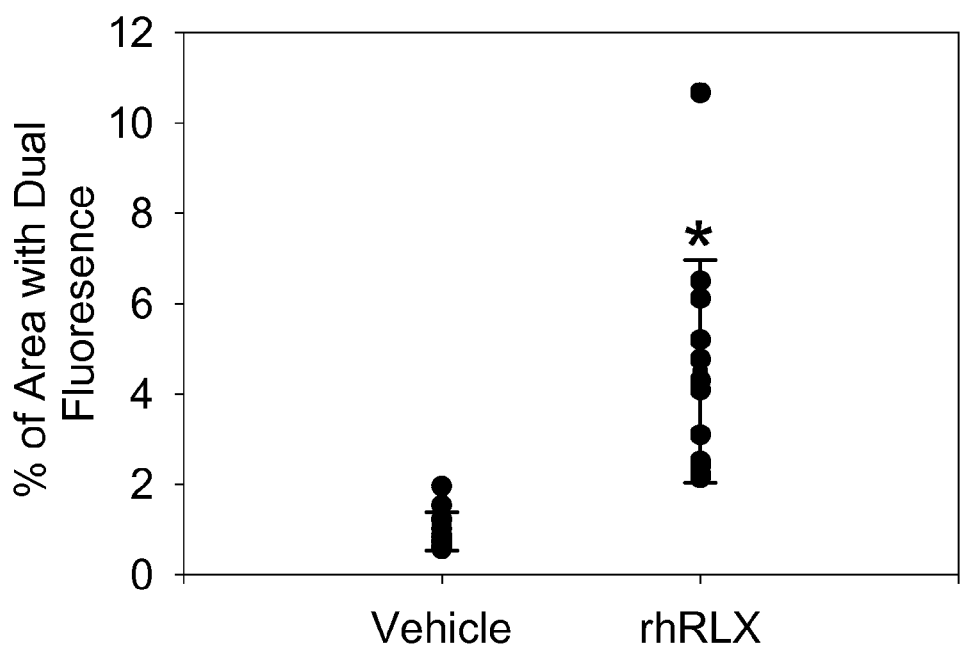

Relaxin stimulates vasculogenesis in vivo. To test whether relaxin will stimulate vasculogenesis and enhance recruitment of BMDEC to sites of vasculogenesis, Matrigel pellets containing rhRLX or its vehicle were inserted subcutaneously in green fluorescent protein (GFP) chimeric mice, in which bone marrow cells and cells derived from the bone marrow selectively express GFP. Pellets impregnated with rhRLX demonstrated a 3.2-fold increase in the mean area of red fluorescence versus pellets containing vehicle (mean area 5.5±4.2% verse 1.7±0.84%, respectively, p<0.001, FIG. 6c), indicating that rhRLX stimulated vasculogenesis. Of note, pellets that contained rhRLX showed a 4.5-fold increase in the mean area of dual fluorescent areas, i.e. cells expressing both GFP and the panendothelial cell antigen, MECA32 (4.5±4.2% verse 0.99±0.84%, respectively, p=0.001, FIG. 6d), indicating an increase in the number of cells derived from the bone marrow that differentiated into endothelial cells (FIG. 6a). Confocal imaging demonstrated blood vessels lined with GFP-positive BMDEC (FIG. 6b), although the different cell localization of the GFP (intracellular) and MECA32 (cell surface) precluded detection of yellow in the merged image by confocal microscopy.

Example 2

One embodiment of the invention is directed to relaxin administration to improve bone fracture healing.

To confirm that relaxin administration accelerates bone healing, chimeric mice stably transplanted with bone marrow harvested from green fluorescent protein (GFP) mice can be used. The calvarial defect model can be implemented and the time course of defect closure analyzed over a 12-week period using micro-computed tomographic images in chimeric mice administered recombinant human relaxin (rhRLX) or vehicle during the initial 2 weeks of healing.

To confirm that relaxin administration mobilizes bone marrow derived angio-osteogenic progenitor cells, circulating bone marrow derived angio-osteogenic progenitor cells can be analyzed by flow cytometry and colony forming assays.

To confirm that relaxin administration associates the bone marrow derived angio-osteogenic progenitor cells with enhanced vasculogenesis and osteogenesis, vascular and osteoblastic density can be measured in regenerating tissue, along with the percentage cells co-expressing GFP.

To confirm that circulating bone marrow derived angio-osteogenic cells facilitate bone healing, chimeric mice stably transplanted with bone marrow harvested from eNOS−/− mice can be used. Incorporation of bone marrow derived progenitor cells lacking endothelial nitric oxide synthase (eNOS) (and eNOS derived NO production) cannot integrate into vasculature [Aicher A et al. 2003. Essential role of endothelial nitric oxide synthase for mobilization of stem and progenitor cells. *Nat Med.* 9:1370-6]. The transplanted bone marrow cells will also be GFP positive.

To confirm the role of relaxin in bone fracture repair in pregnancy and the non-pregnant condition, relaxin knock-out mice (pregnant and non-pregnant) can be studied.

It is expected that rhRLX accelerates closure of the calvarial defect. The enhanced bone healing by rhRLX is associated with increased circulating angio-osteoblastic cells, which traffic to and are incorporated into the bone defect site, thereby abetting repair. It is also expected that defective incorporation of eNOS$^{-/-}$ angio-osteoblastic cells in the calvarial lesion will result in delayed closure.

Example 3

In addition, the subject methods may be used to treat avascular necrosis seen in patients with lupus. It has previously been demonstrated that patients with lupus who have higher interferon alpha levels (approximately 50% of the lupus population) have diminished bone marrow derived angiogenic cells and that interferon alpha directly affects bone marrow derived angiogenic cell survival [Li Y et al., 2010. Monocyte surface expression of Fcgamma receptor RI (CD64), a biomarker reflecting type-I interferon levels in systemic lupus erythematosus. *Arthritis Res Ther.* 12:R90]. The methods for stimulating BMDEC as described herein can treat lupus patients, particularly avascular necrosis seen in lupus patients with higher interferon alpha levels.

Example 4

Further, the subject methods can be used in treating pancreatic beta-cell injury. Mathews et al. [2004. Recruitment of bone marrow-derived endothelial cells to sites of pancreatic beta-cell injury. *Diabetes.* 53(1):91-8] demonstrated that BMDECs were recruited to the pancreas in response to islet injury. The methods for stimulating BMDEC as described herein can treat transplant patients, particularly patients receiving islet and/or pancreas allografts where BMDEC mediated neovascularization can facilitate the recovery of non-terminally injured beta-cells.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for stimulating bone marrow-derived endothelial cell (BMDEC) mobilization and integration in a subject having been diagnosed with a disease or condition caused or made worse by insufficient vasculogenesis, wherein said method comprises administering, to the subject in need of such BMDEC mobilization and integration, an amount of relaxin effective to stimulate BMDEC mobilization and integration, and collecting the peripheral blood of the subject to evaluate BMDEC mobilization and integration, and wherein the disease or condition is selected from the group consisting of muscular dystrophy, neonatal respiratory distress syndrome, and organ transplantation.

2. The method of claim 1, wherein the relaxin induces an increase in BMDEC activity and/or an increase in BMDEC nitric oxide production.

3. The method of claim 2, wherein BMDEC activity includes BMDEC proliferation and/or migration.

4. The method of claim 1, wherein the administration is selected from one of the following: local, systemic, oral, parenteral, intramuscular, and intravascular.

5. The method of claim 1, wherein the relaxin is effective in preserving function and long-term patency of a dialysis access.

6. The method of claim 1, wherein the relaxin is effective to increase blood flow, promote vasculogenesis and/or promote vessel regeneration.

7. The method of claim 1, wherein the subject has had organ transplantation.

8. A method for stimulating bone marrow-derived endothelial cell (BMDEC) mobilization and integration in a subject having been diagnosed with muscular dystrophy, wherein said method comprises administering, to the subject in need of such BMDEC mobilization and integration, an amount of relaxin effective to stimulate BMDEC mobilization and integration.

9. The method of claim 8, wherein the relaxin induces an increase in BMDEC activity and/or an increase in BMDEC nitric oxide production.

10. The method of claim 8, wherein BMDEC activity includes BMDEC proliferation and/or migration.

11. The method of claim 8, wherein the administration is selected from one of the following: local, systemic, oral, parenteral, intramuscular, and intravascular.

12. A method for stimulating bone marrow-derived endothelial cell (BMDEC) mobilization and integration in a subject having been diagnosed with neonatal respiratory distress syndrome, wherein said method comprises administering, to the subject in need of such BMDEC mobilization and integration, an amount of relaxin effective to stimulate BMDEC mobilization and integration.

13. The method of claim 12, wherein the relaxin induces an increase in BMDEC activity and/or an increase in BMDEC nitric oxide production.

14. The method of claim 12, wherein BMDEC activity includes BMDEC proliferation and/or migration.

15. The method of claim 12, wherein the administration is selected from one of the following: local, systemic, oral, parenteral, intramuscular, and intravascular.

* * * * *